United States Patent
Payan et al.

(10) Patent No.: US 6,316,223 B1
(45) Date of Patent: Nov. 13, 2001

(54) MAMMALIAN PROTEIN INTERACTION CLONING SYSTEM

(75) Inventors: Donald Payan, Hillsborough; Ying Luo, Los Altos; Betty Huang, San Leandro, all of CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/359,081

(22) Filed: Jul. 22, 1999

Related U.S. Application Data

(63) Continuation-in-part of application No. 09/050,863, filed on Mar. 30, 1998, now Pat. No. 6,114,111.

(51) Int. Cl.⁷ .............................. C12P 21/06; C12P 21/04

(52) U.S. Cl. ......................................... 435/69.1; 435/70.1

(58) Field of Search ................................... 435/69.1, 70.1

(56) References Cited

U.S. PATENT DOCUMENTS

| | | | |
|---|---|---|---|
| 5,139,941 | 8/1992 | Muzyczka et al. | 435/172.3 |
| 5,283,173 | 2/1994 | Fields et al. | 435/6 |
| 5,468,614 | 11/1995 | Fields et al. | 435/6 |
| 5,525,490 | 6/1996 | Erickson et al. | 435/29 |
| 5,637,463 | 6/1997 | Dalton et al. | 435/6 |
| 5,667,973 | 9/1997 | Fields et al. | 435/6 |

FOREIGN PATENT DOCUMENTS

| 97/31113 | 8/1997 | (WO) . |
|---|---|---|

OTHER PUBLICATIONS

Fields and Song, "A novel genetic system to detect protein–protein interactions," *Nature*, 340: 245–246 (Jul. 1989).

Fearon et al., "Karyoplasmic interaction selection strategy: A general strategy to detect protein–protein interactions in mammalian cells," *Proc. Natl. Acad. Sci. USA*, 89:7958–7962 (Sep. 1992).

Dang et al., "Intracellular Leucine Zipper Interactions Suggest c–Myc Hetero–Oligomerization," *Molecular and Cellular Biology*, 1(2):954–962 (Feb. 1991).

Chien et al., "The two–hybrid system: A method to identify and clone genes for proteins that interact with a protein of interest," *Proc. Natl. Acad. Sci. USA*, 88:9578–9582 (Nov. 1991).

(List continued on next page.)

*Primary Examiner*—Hankyel T. Park
(74) *Attorney, Agent, or Firm*—Flehr Hohbach Test Albritton & Herbert LLP; Robin M. Silva

(57) ABSTRACT

The present invention is directed to compositions and methods for a genetic system of detecting protein-protein interactions in a mammalian host cell. Two fusion proteins are made in the host cell. The first fusion protein contains a DNA binding domain which is fused to a so-called bait protein. The second fusion protein consists of a transcriptional activation domain fused to a so-called test protein. The DNA binding domain binds to an operator sequence which controls expression of one or more reporter genes. The transcriptional activation domain is recruited to the promoter through the functional interaction between the bait protein and the test protein. Subsequently the transcriptional activation domain interacts with the basal transcription machinery to activate expression of one or more reporter genes which can be identified and characterized. The individual compositions are useful for analyzing protein-protein interactions between known proteins and to isolate, clone and characterize unknown proteins. The individual compositions can be used to express the fusion proteins either transiently or stably. In addition, the present invention is directed to methods for screening for candidate bioactive agents that modulate the protein-protein interaction between a bait protein and a test protein and thus are useful for the identification of novel therapeutic drugs and the like.

11 Claims, 9 Drawing Sheets-

OTHER PUBLICATIONS

Vasavada et al., "A contingent replication assay for the detection of protein–protein interactions in animal cells," *Proc. Natl. Acad. Sci. USA* 88:10686–10690 (Dec. 1991).

Luo et al., "Mammalian two–hybrid system: a complementary approach to the yeast two–hybrid system" *Biotechniques*, 22(2):350–352 (Feb. 1997).

Richardson et al., "vRel is an inactive member of the Rel family of transcriptional activating proteins," *J. Virol.*, 65(6):3122–3130 (Jun. 1991).

Mann et al., "Construction of a retrovirus packaging mutant and its use to produce helper–free defective retrovirus," *Cell*, 33(1):153–159 (May 1983).

Pear et al., "Production of high–titer helper–free retroviruses by transient transfection," *Proc. Natl. Acad. Sci. USA*, 90(18):8392–8396 (Sep. 1993).

Kitamura et al., "Efficient screening of retroviral cDNA expression libraries," *Proc. Natl. Acad. Sci. USA*, 92(20):9146–9150 (Sep. 1995).

Kinsella et al., "Episomal vectors rapidly and stably produce high–titer recombinant viruses," *Hum. Gene Ther.*, 7(12):1405–1413 (Aug. 1996).

Hofmann et al., "Rapid retroviral delivery of tetracycline–inducible genes in a single autoregulatory cassette," *Proc. Natl. Acad. Sci. USA*, 93(11):5185–5190 (May 1996).

Choate et al., "Transglutaminase 1 delivery to lamella ichthyosis keratinocytes," *Hum. Gene Ther.*, 7(18):2247–2253 (Dec. 1996).

Gossen et al., "Tight control of gene expression in mammalian cells by tetracycline–responsive promoters," *Proc. Natl. Acad. Sci. USA*, 89(12):5547–5551 (Jun. 1992).

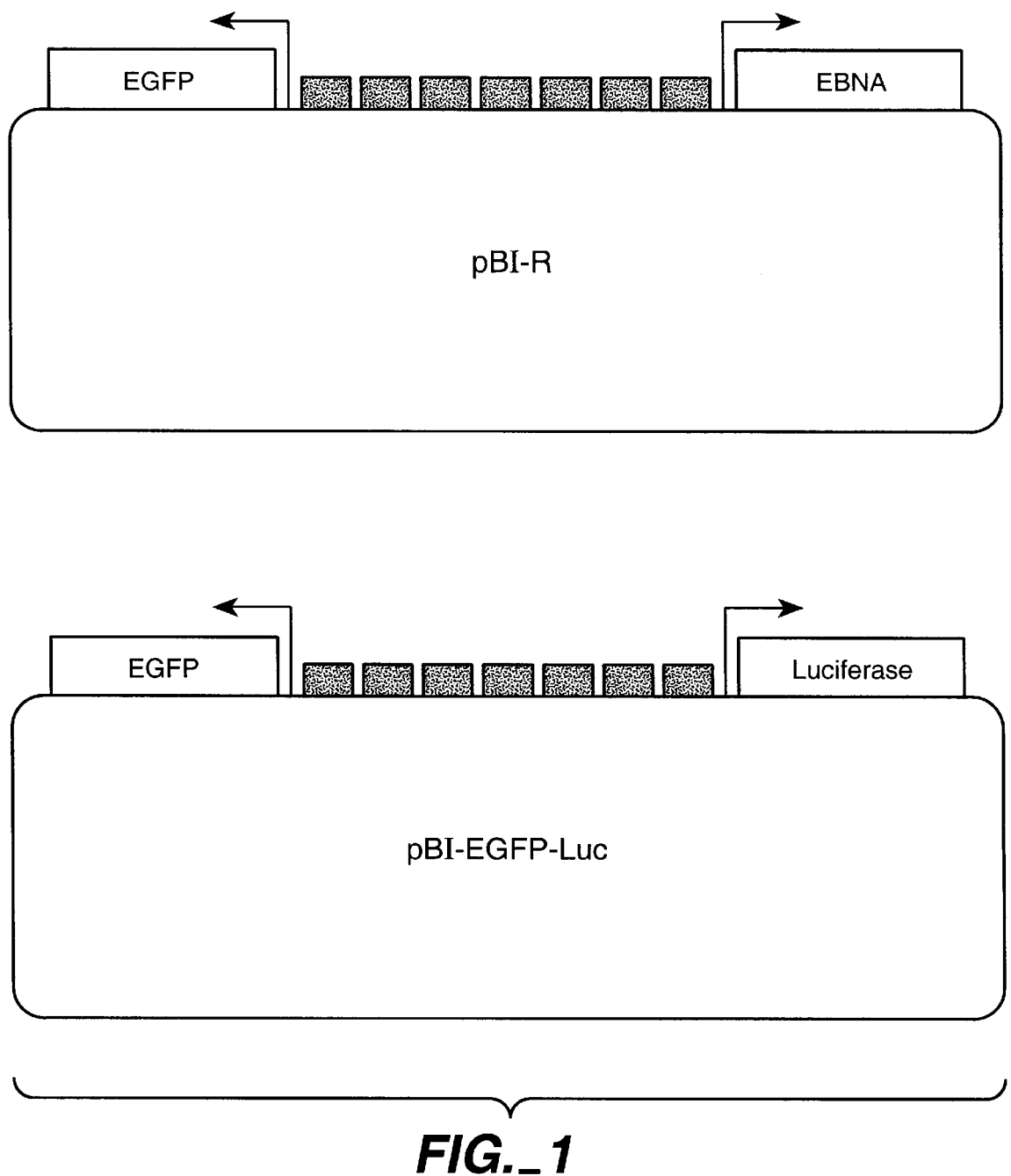
FIG._1

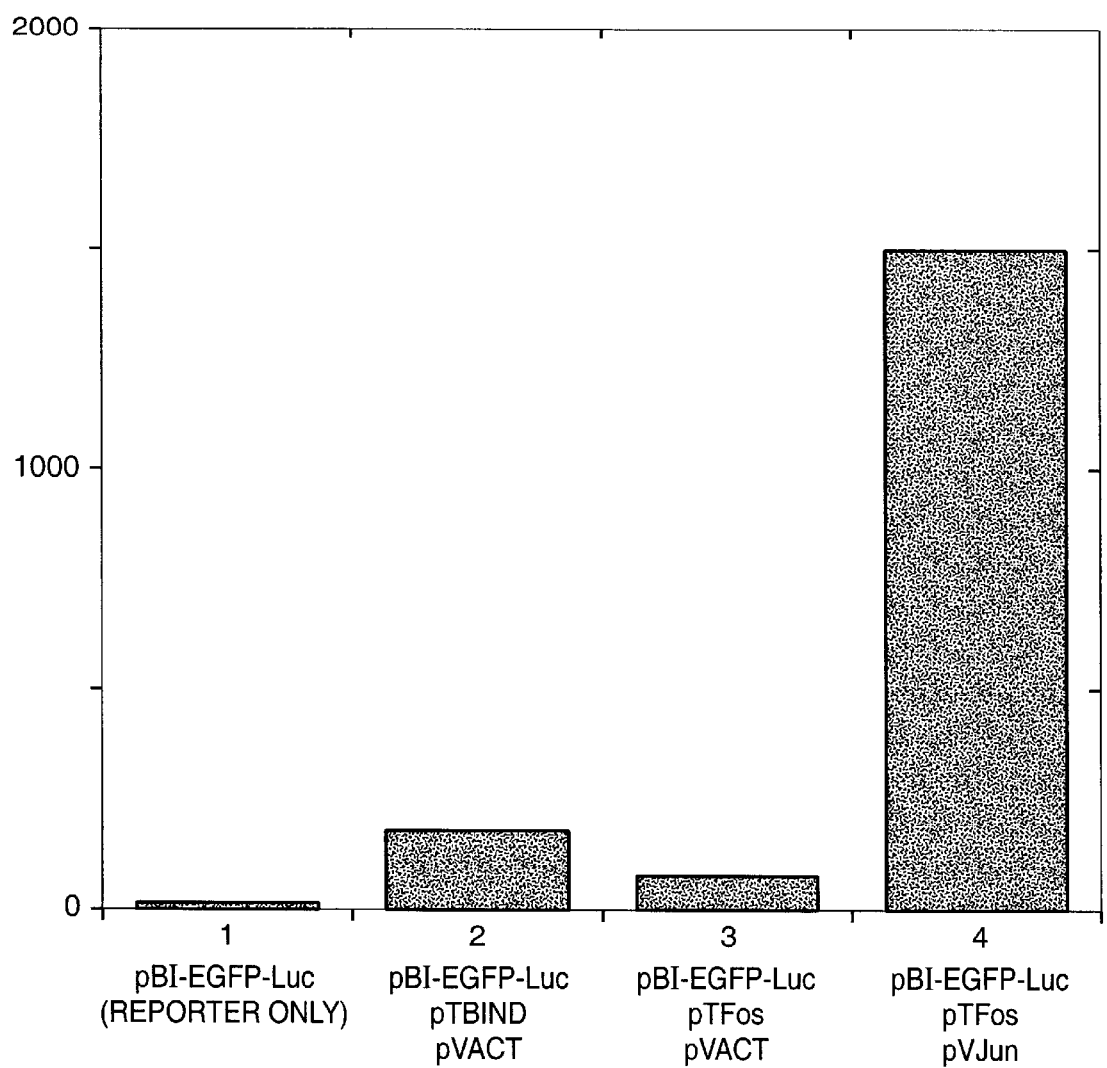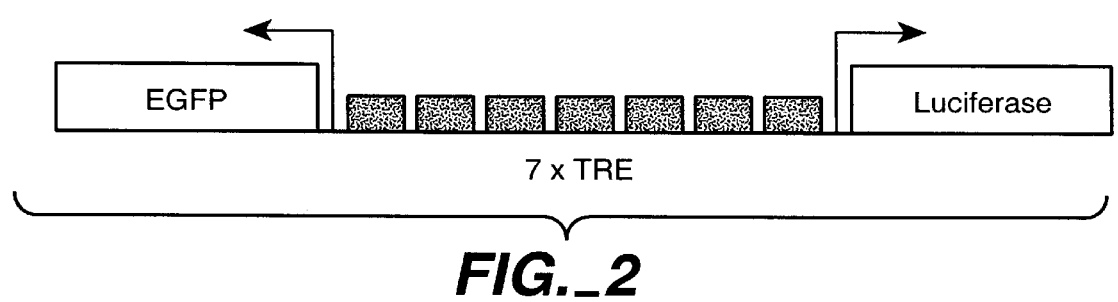
FIG._2

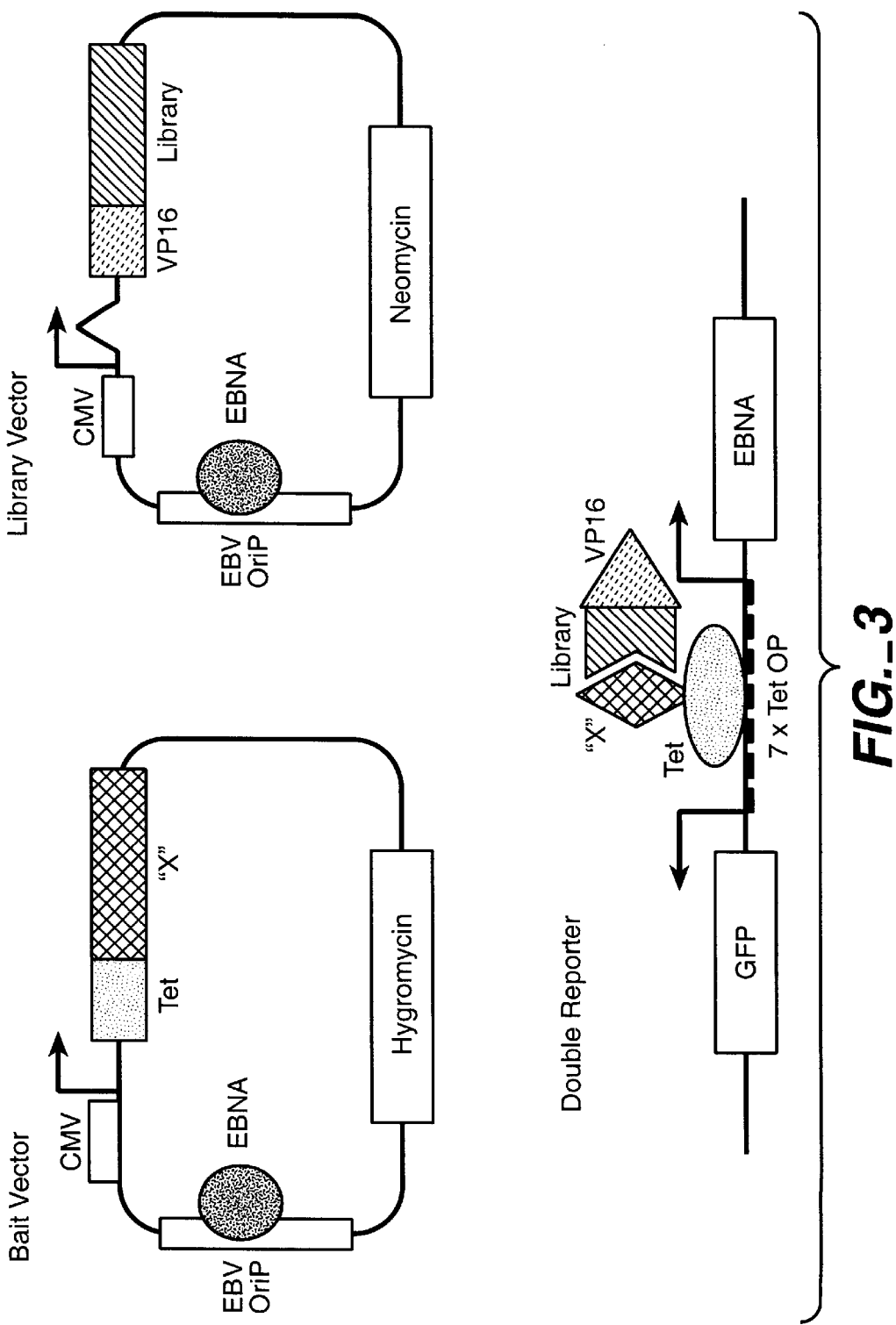
FIG._3

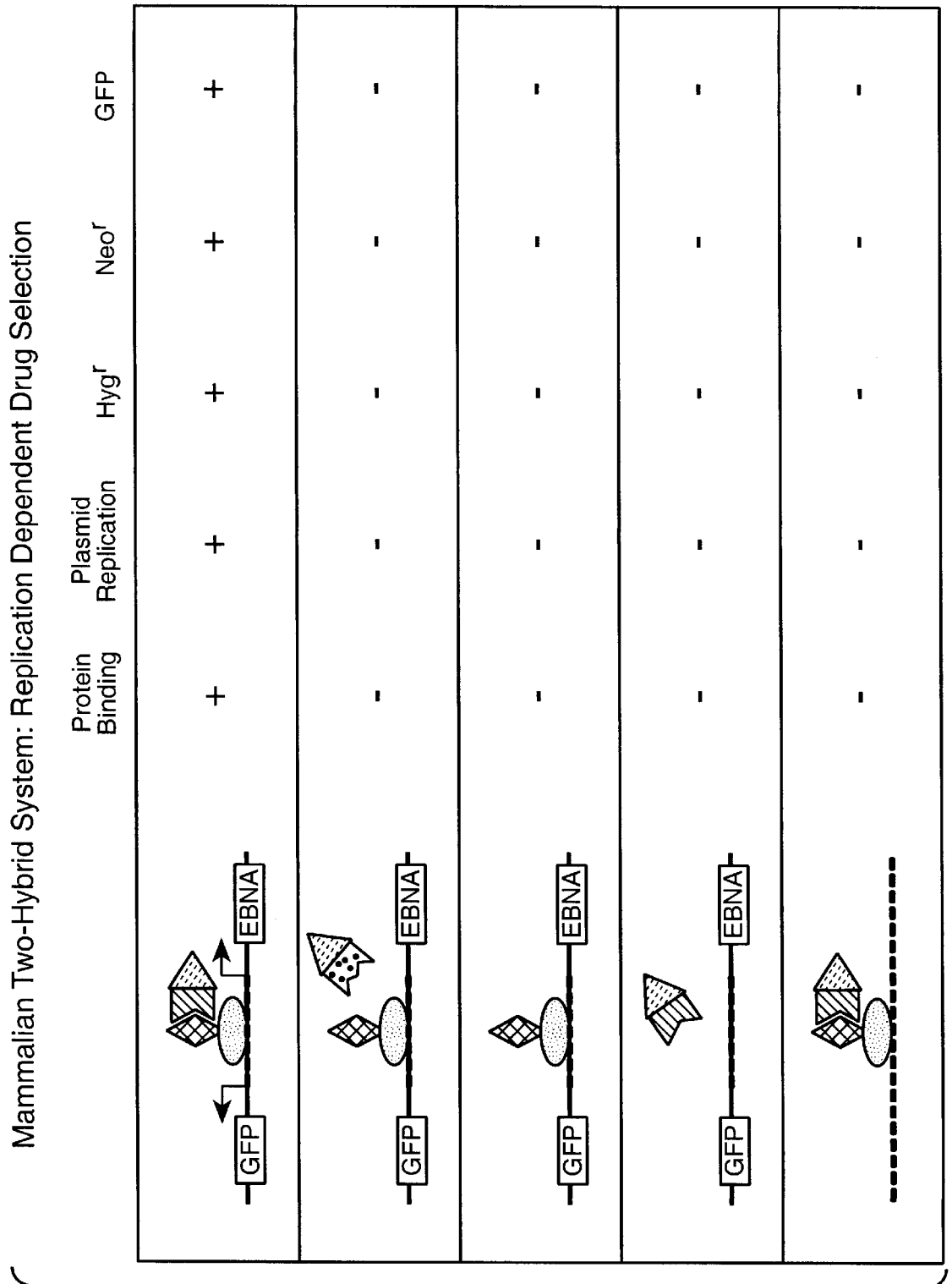
FIG._4

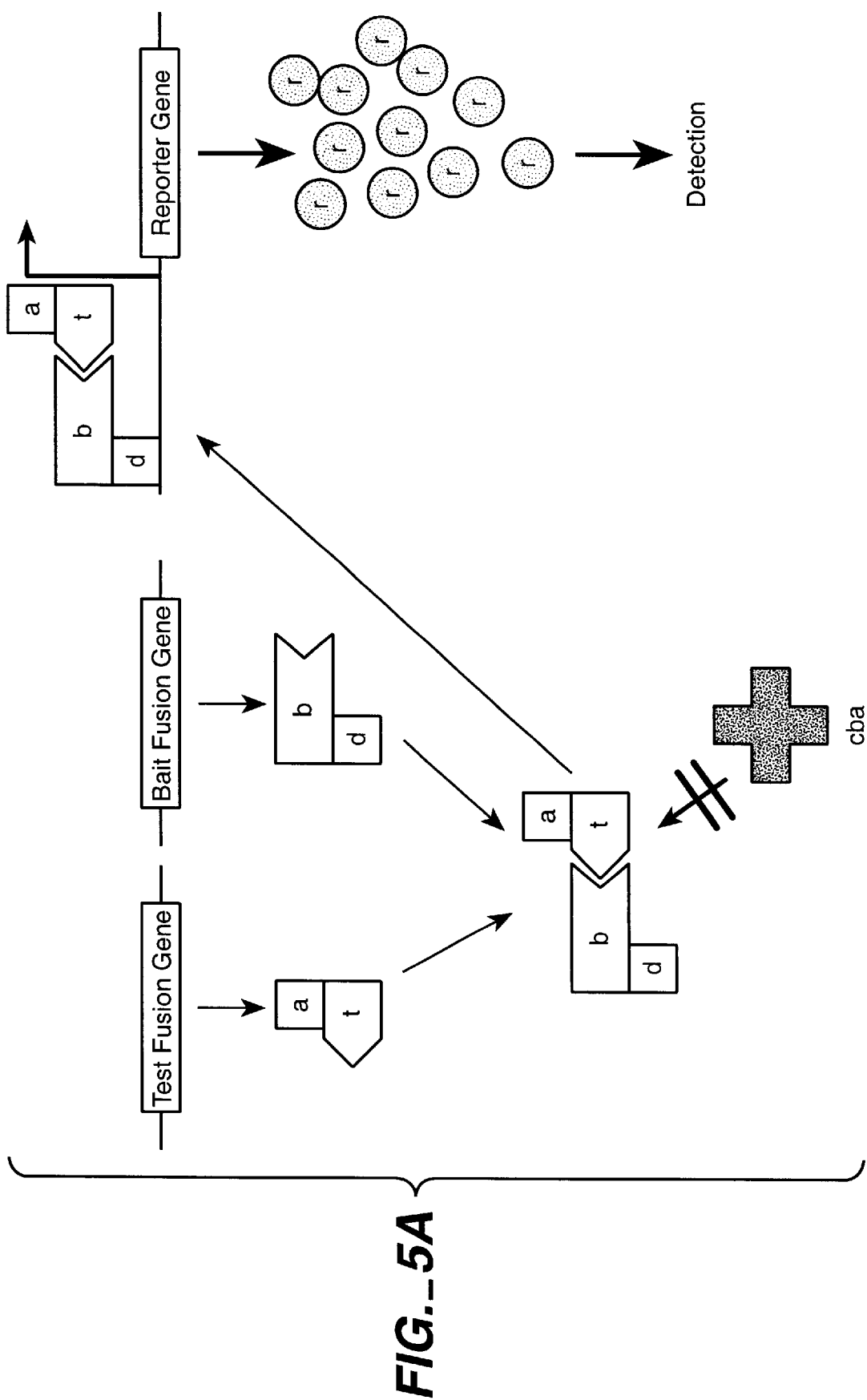
FIG._5A

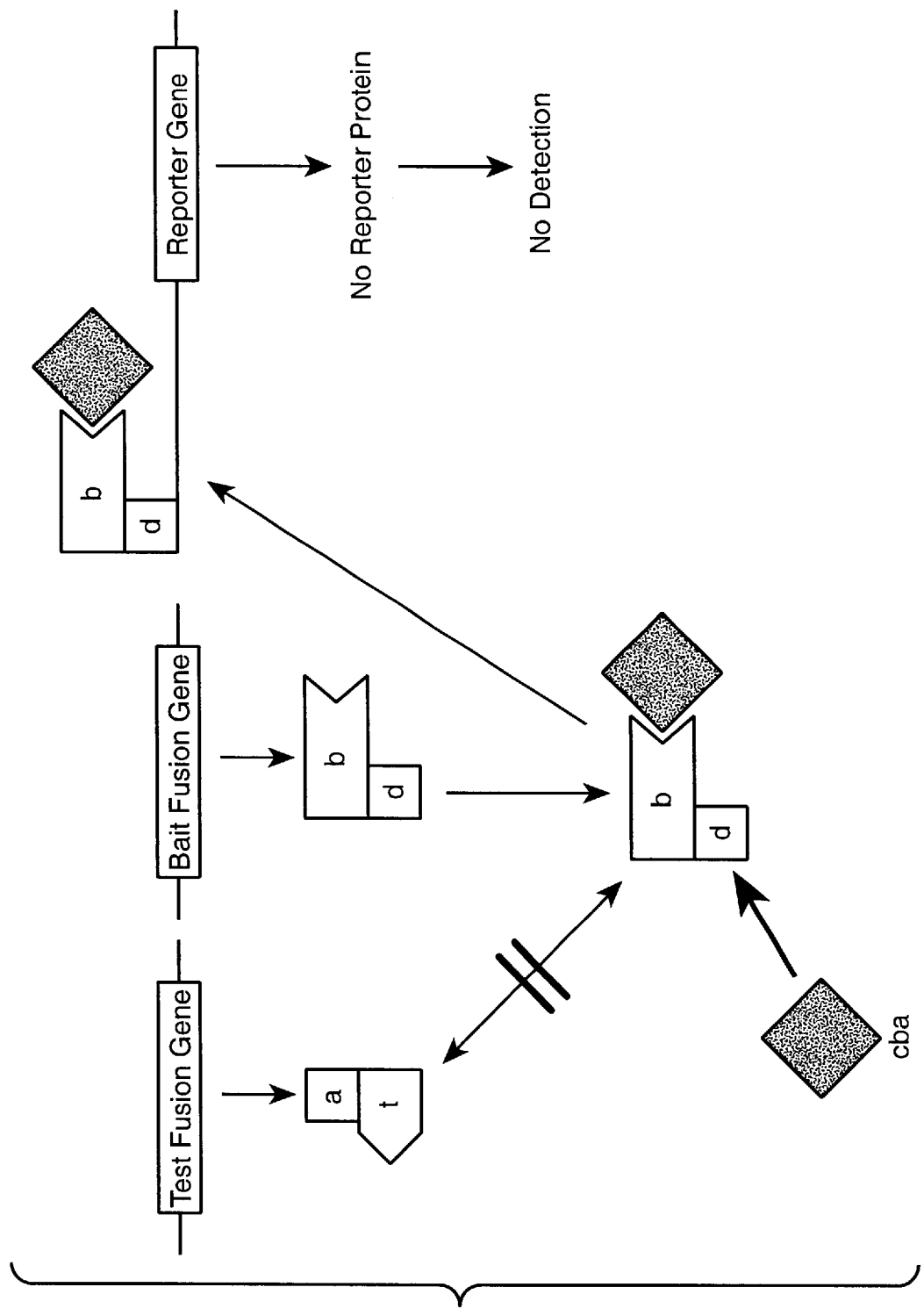
FIG._5B

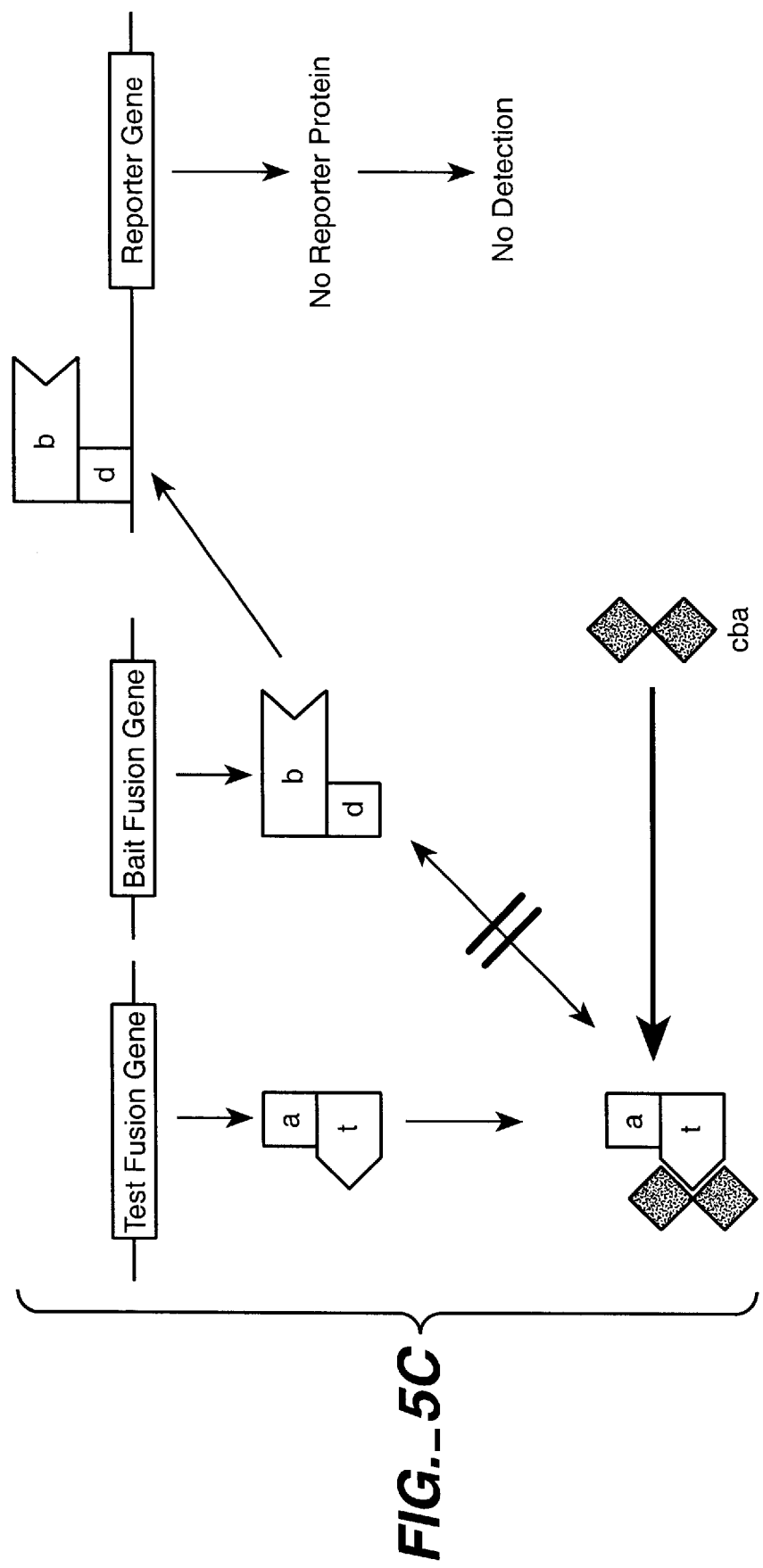
FIG._5C

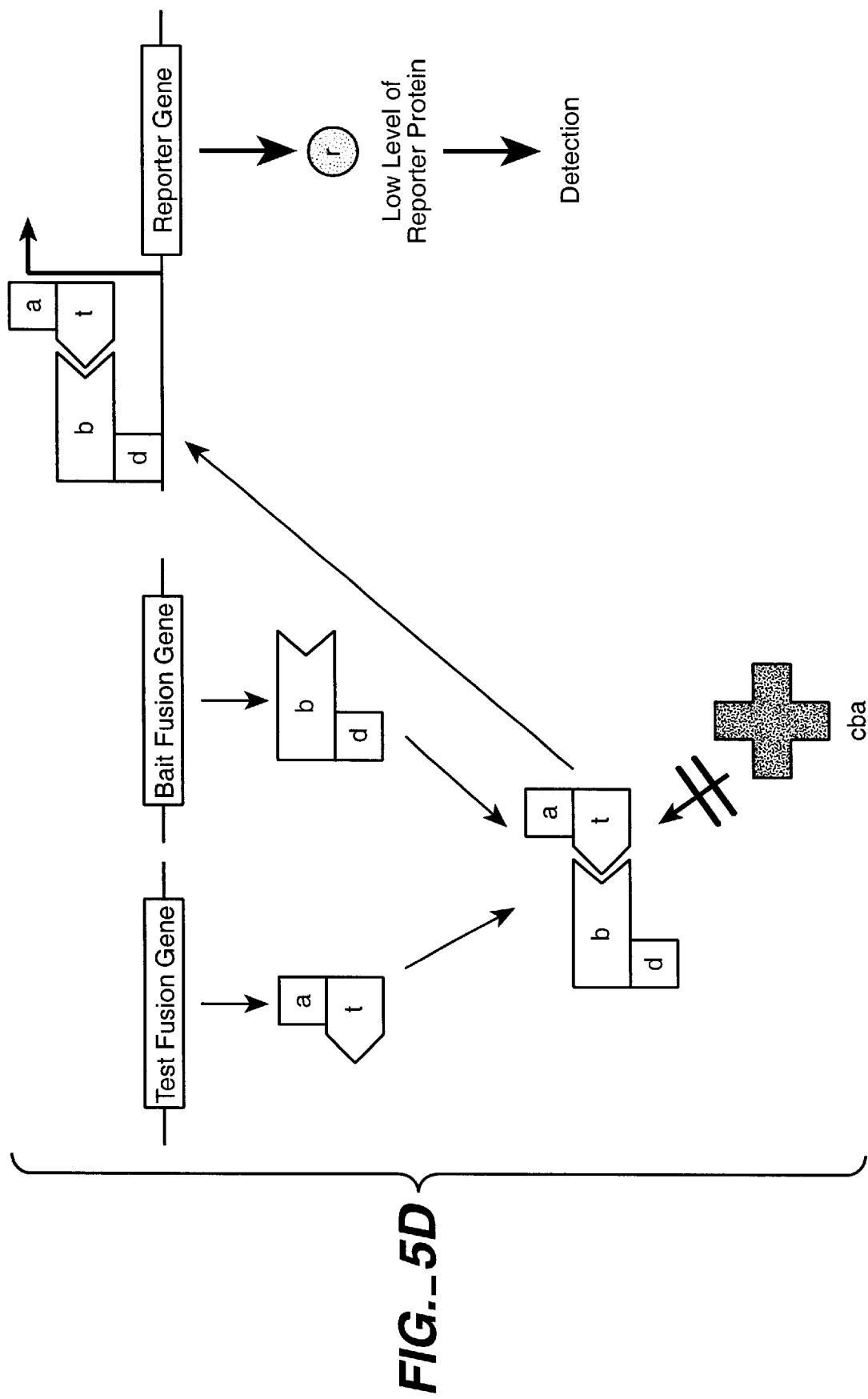
FIG._5D

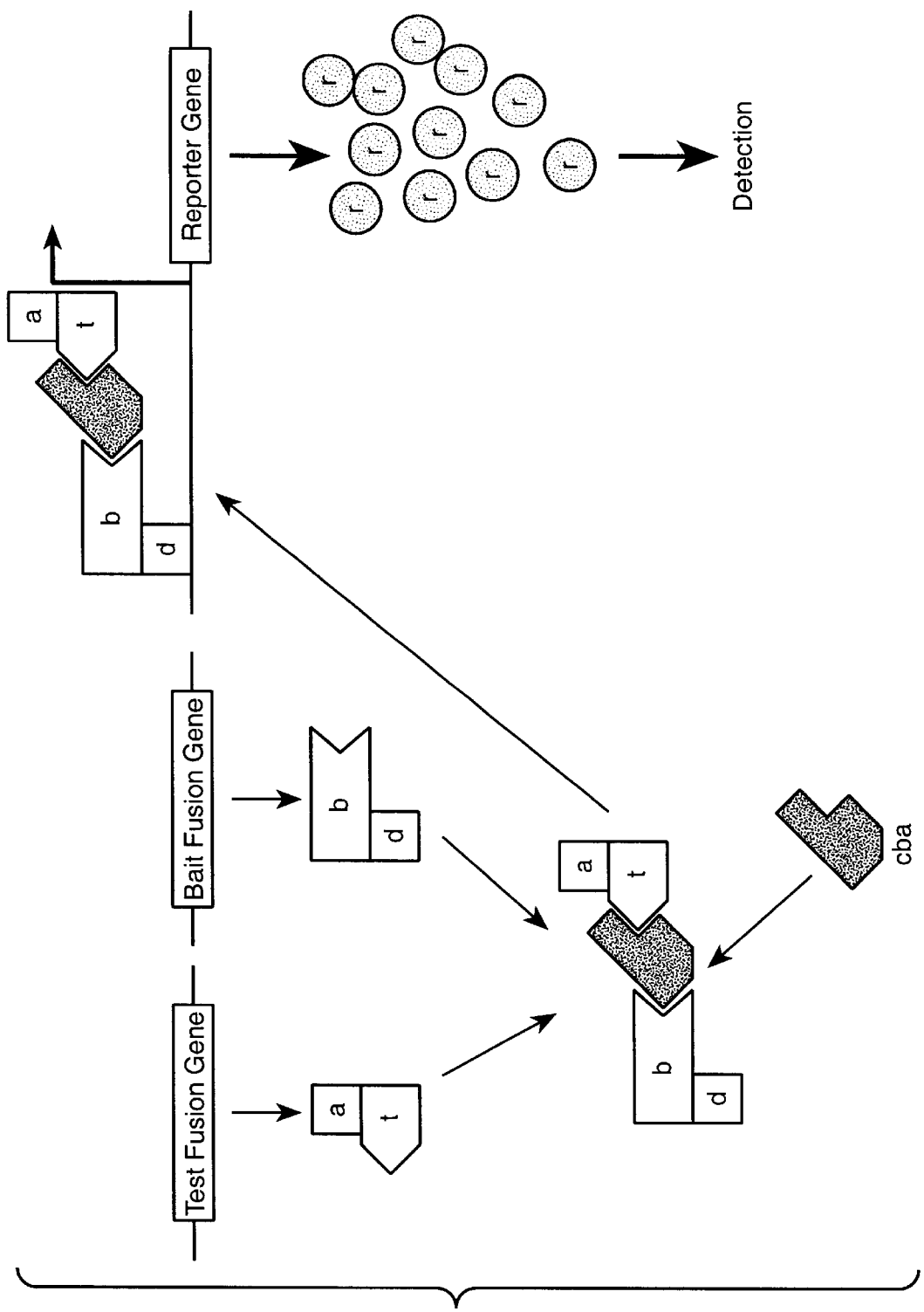
FIG._5E

```
                              SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
          (A) LENGTH: 1937 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO: 1:

GCATGCAGGA AAAGGACAAG CAGCGAAAAT TCACGCCCCC TTGGGAGGTG GCGGCATATG      60

CAAAGGATAG CACTCCCACT CTACTACTGG GTATCATATG CTGACTGTAT ATGCATGAGG     120

ATAGCATATG CTACCCGGAT ACAGATTAGG ATAGCATATA CTACCCAGAT ATAGATTAGG     180

ATAGCATATG CTACCCAGAT ATAGATTAGG ATAGCCTATG CTACCCAGAT ATAAATTAGG     240

ATAGCATATA CTACCCAGAT ATAGATTAGG ATAGCATATG CTACCCAGAT ATAGATTAGG     300

ATAGCCTATG CTACCCAGAT ATAGATTAGG ATAGCATATG CTACCCAGAT ATAGATTAGG     360

ATAGCATATG CTATCCAGAT ATTTGGGTAG TATATGCTAC CCAGATATAA ATTAGGATAG     420

CATATACTAC CCTAATCTCT ATTAGGATAG CATATGCTAC CCGGATACAG ATTAGGATAG     480
```

-continued

```
CATATACTAC CCAGATATAG ATTAGGATAG CATATGCTAC CCAGATATAG ATTAGGATAG      540

CCTATGCTAC CCAGATATAA ATTAGGATAG CATATACTAC CCAGATATAG ATTAGGATAG      600

CATATGCTAC CCAGATATAG ATTAGGATAG CCTATGCTAC CCAGATATAG ATTAGGATAG      660

CATATGCTAT CCAGATATTT GGGTAGTATA TGCTACCCAT GGCAACATTA GCCCACCGTG      720

CTCTCAGCGA CCTCGTGAAT ATGAGGACCA ACAACCCTGT GCTTGGCGCT CAGGCGCAAG      780

TGTGTGTAAT TTGTCCTCCA GATCGCAGCA ATCGCGCCCC TATCTTGGCC CGCCCACCTA      840

CTTATGCAGG TATTCCCCGG GGTGCCATTA GTGGTTTTGT GGGCAAGTGG TTTGACCGCA      900

GTGGTTAGCG GGGTTACAAT CAGCCAAGTT ATTACACCCT TATTTTACAG TCCAAAACCG      960

CAGGGCGGCG TGTGGGGGCT GACGCGTGCC CCCACTCCAC AATTTCAAAA AAAAGAGTGG     1020

CCACTTGTCT TTGTTTATGG GCCCCATTGG CGTGGAGCCC CGTTTAATTT TCGGGGGTGT     1080

TAGAGACAAC CAGTGGAGTC CGCTGCTGTC GGCGTCCACT CTCTTTCCCC TTGTTACAAA     1140

TAGAGTGTAA CAACATGGTT CACCTGTCTT GGTCCCTGCC TGGGACACAT CTTAATAACC     1200

CCAGTATCAT ATTGCACTAG GATTATGTGT TGCCCATAGC CATAAATTCG TGTGAGATGG     1260

ACATCCAGTC TTTACGGCTT GTCCCCACCC CATGGATTTC TATTGTTAAA GATATTCAGA     1320

ATGTTTCATT CCTACACTAG TATTTATTGC CCAAGGGGTT TGTGAGGGTT ATATTGGTGT     1380

CATAGCACAA TGCCACCACT GAACCCCCCG TCCAAATTTT ATTCTGGGGG CGTCACCTGA     1440

AACCTTGTTT TCGAGCACCT CACATACACC TTACTGTTCA CAACTCAGCA GTTATTCTAT     1500

TAGCTAAACG AAGGAGAATG AAGAAGCAGG CGAAGATTCA GGAGAGTTCA CTGCCCGCTC     1560

CTTGATCTTC AGCCACTGCC CTTGTGACTA AAATGGTTCA CTACCCTCGT GGAATCCTGA     1620

CCCCATGTAA ATAAAACCGT GACAGCTCAT GGGGTGGGAG ATATCGCTGT TCCTTAGGAC     1680

CCTTTTACTA ACCCTAATTC GATAGCATAT GCTTCCCGTT GGGTAACATA TGCTATTGAA     1740

TTAGGGTTAG TCTGGATAGT ATATACTACT ACCCGGGAAG CATATGCTAC CCGTTTAGGG     1800

TTAACAAGGG GGCCTTATAA ACACTATTGC TAATGCCCTC TTGAGGGTCC GCTTATCGGT     1860

AGCTACACAG GCCCCTCTGA TTGACGTTGG TGTAGCCTCC CGTAGTCTTC CTGGGCCCCT     1920

GGGAGGTACA TGTCCCC                                                   1937
```

(2) INFORMATION FOR SEQ ID NO: 2:

(i) SEQUENCE CHARACTERISTICS:
        (A) LENGTH: 2580 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 2:

```
ATCCTCACAG GCCGCACCCA GCTTTTCTTC CGTTGCCCCA GTAGCATCTC TGTCTGGTGA       60

CCTTGAAGAG GAAGAGGAGG GGTCCCGAGA ATCCCCATCC CTACCGTCCA GCAAAAAGGG      120

GGACGAGGAA TTTGAGGCCT GGCTTGAGGC TCAGGACGCA AATCTTGAGG ATGTTCAGCG      180

GGAGTTTTCC GGGCTGCGAG TAATTGGTGA TGAGGACGAG GATGGTTCGG AGGATGGGGA      240

ATTTTCAGAC CTGGATCTGT CTGACAGCGA CCATGAAGGG GATGAGGGTG GGGGGGCTGT      300

TGGAGGGGGC AGGAGTCTGC ACTCCCTGTA TTCACTGAGC GTCGTCTAAT AAAGATGTCG      360

ATTGATCTCT TTTAGTGTGA ATCATGTCTG ACGAGGGGCC AGGTACAGGA CCTGGAAATG      420

GCCTAGGAGA GAAGGGAGAC ACATCTGGAC CAGAAGGCTC CGGCGGCAGT GGACCTCAAA      480
```

```
GAAGAGGGGG TGATAACCAT GGACGAGGAC GGGGAAGAGG ACGAGGACGA GGAGGCGGAA    540

GACCAGGAGC CCCGGGCGGC TCAGGATCAG GGCCAAGACA TAGAGATGGT GTCCGGAGAC    600

CCCAAAAACG TCCAAGTTGC ATTGGCTGCA AAGGGACCCA CGGTGGAACA GGAGCAGGAG    660

CAGGAGCGGG AGGGGCAGGA GCAGGAGGGG CAGGAGCAGG AGGAGGGGCA GGAGCAGGAG    720

GAGGGGCAGG AGGGGCAGGA GGGGCAGGAG GGCAGGAGC AGGAGGAGGG GCAGGAGCAG    780

GAGGAGGGGC AGGAGGGGCA GGAGGGGCAG GAGCAGGAGG AGGGGCAGGA GCAGGAGGAG    840

GGGCAGGAGG GGCAGGAGCA GGAGGAGGGG CAGGAGGGGC AGGAGGGGCA GGAGCAGGAG    900

GAGGGGCAGG AGCAGGAGGA GGGCAGGAG GGCAGGAGC AGGAGGAGGG GCAGGAGGGG    960

CAGGAGGGGC AGGAGCAGGA GGAGGGGCAG GAGCAGGAGG GGCAGGAGGG GCAGGAGGGG   1020

CAGGAGCAGG AGGGGCAGGA GCAGGAGGAG GGGCAGGAGG GGCAGGAGGG GCAGGAGCAG   1080

GAGGGGCAGG AGCAGGAGGG GCAGGAGCAG GAGGGGCAGG AGCAGGAGGG GCAGGAGGGG   1140

CAGGAGCAGG AGGGGCAGGA GGGGCAGGAG CAGGAGGGGC AGGAGGGGCA GGAGCAGGAG   1200

GAGGGGCAGG AGGGGCAGGA GCAGGAGGAG GGGCAGGAGG GGCAGGAGCA GGAGGGGCAG   1260

GAGGGGCAGG AGCAGGAGGG GCAGGAGGGG CAGGAGCAGG AGGGGCAGGA GGGGCAGGAG   1320

CAGGAGGAGG GGCAGGAGCA GGAGGGGCAG GAGCAGGAGG TGGAGGCCGG GGTCGAGGAG   1380

GCAGTGGAGG CCGGGGTCGA GGAGGTAGTG GAGGCCGGGG TCGAGGAGGT AGTGGAGGCC   1440

GCCGGGGTAG AGGACGTGAA AGAGCCAGGG GGGGAAGTCG TGAAAGAGCC AGGGGGAGAG   1500

GTCGTGGACG TGGAGAAAAG AGGCCCAGGA GTCCCAGTAG TCAGTCATCA TCATCCGGGT   1560

CTCCACCGCG CAGGCCCCCT CCAGGTAGAA GGCCATTTTT CCACCCTGTA GGGGAAGCCG   1620

ATTATTTTGA ATACCACCAA GAAGGTGGCC CAGATGGTGA GCCTGACGTG CCCCCGGGAG   1680

CGATAGAGCA GGGCCCCGCA GATGACCCAG GAGAAGGCCC AAGCACTGGA CCCCGGGGTC   1740

AGGGTGATGG AGGCAGGCGC AAAAAAGGAG GGTGGTTTGG AAAGCATCGT GGTCAAGGAG   1800

GTTCCAACCC GAAATTTGAG AACATTGCAG AAGGTTTAAG AGCTCTCCTG GCTAGGAGTC   1860

ACGTAGAAAG GACTACCGAC GAAGGAACTT GGGTCGCCGG TGTGTTCGTA TATGGAGGTA   1920

GTAAGACCTC CCTTTACAAC CTAAGGCGAG GAACTGCCCT TGCTATTCCA CAATGTCGTC   1980

TTACACCATT GAGTCGTCTC CCCTTTGGAA TGGCCCCTGG ACCCGGCCCA CAACCTGGCC   2040

CGCTAAGGAG TCCATTGTCT GTTATTTCAT GGTCTTTTTA CAAACTCATA TATTTGCTGA   2100

GGTTTTGAAG GATGCGATTA AGGACCTTGT TATGACAAAG CCCGCTCCTA CCTGCAATAT   2160

CAGGGTGACT GTGTGCAGCT TTGACGATGG AGTAGATTTG CCTCCCTGGT TTCCACCTAT   2220

GGTGGAAGGG GCTGCCGCGG AGGGTGATGA CGGAGATGAC GGAGATGAAG GAGGTGATGG   2280

AGATGAGGGT GAGGAAGGGC AGGAGTGATG TAACTTGTTA GGAGACGCCC TCAATCGTAT   2340

TAAAAGCCGT GTATTCCCCC GCACTAAAGA ATAAATCCCC AGTAGACATC ATGCGTGCTG   2400

TTGGTGTATT TCTGGCCATC TGTCTTGTCA CCATTTTCGT CCTCCCAACA TGGGGCAATT   2460

GGGCATACCC ATGTTGTCAC GTCACTCAGC TCCGCGCTCA ACACCTTCTC GCGTTGGAAA   2520

ACATTAGCGA CATTTACCTG GTGAGCAATC AGACATGCGA CGGCTTTAGC CTGGCCTCCT   2580
```

(2) INFORMATION FOR SEQ ID NO: 3:

(i) SEQUENCE CHARACTERISTICS:
        (A) LENGTH: 66 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 3:

| | | | | | |
|---|---|---|---|---|---|
| AATTTTTTTT | ATTTATGCAG | AGGCCGAGGC | CGCCTCGGCC | TCTGAGCTAT | TCCAGAAGTA | 60 |
| GTGAGG | | | | | 66 |

(2) INFORMATION FOR SEQ ID NO: 4:

(i) SEQUENCE CHARACTERISTICS:
        (A) LENGTH: 2479 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 4:

| | | | | | |
|---|---|---|---|---|---|
| TTATGTTTCA | GGTTCAGGGG | GAGGTGTGGG | AGGTTTTTTA | AAGCAAGTAA | AACCTCTACA | 60 |
| AATGTGGTAT | GGCTGATTAT | GATCATGAAC | AGACTGTGAG | GACTGAGGGG | CCTGAAATGA | 120 |
| GCCTTGGGAC | TGTGAATCAA | TGCCTGTTTC | ATGCCCTGAG | TCTTCCATGT | TCTTCTCCCC | 180 |
| ACCATCTTCA | TTTTTATCAG | CATTTTCCTG | GCTGTCTTCA | TCATCATCAT | CACTGTTTCT | 240 |
| TAGCCAATCT | AAAACTCCAA | TTCCCATAGC | CACATTAAAC | TTCATTTTTT | GATACACTGA | 300 |
| CAAACTAAAC | TCTTTGTCCA | ATCTCTCTTT | CCACTCCACA | ATTCTGCTCT | GAATACTTTG | 360 |
| AGCAAACTCA | GCCACAGGTC | TGTACCAAAT | TAACATAAGA | AGCAAAGCAA | TGCCACTTTG | 420 |
| AATTATTCTC | TTTTCTAACA | AAAACTCACT | GCGTTCCAGG | CAATGCTTTA | AATAATCTTT | 480 |
| GGGCCTAAAA | TCTATTTGTT | TTACAAATCT | GGCCTGCAGT | GTTTTAGGCA | CACTGTACTC | 540 |
| ATTCATGGTG | ACTATTCCAG | GGGGAAATAT | TTGAGTTCTT | TTATTTAGGT | GTTTCTTTTC | 600 |
| TAAGTTTACC | TTAACACTGC | CATCCAAATA | ATCCCTTAAA | TTGTCCAGGT | TATTAATTCC | 660 |
| CTGACCTGAA | GGCAAATCTC | TGGACTCCCC | TCCAGTGCCC | TTTACATCCT | CAAAAACTAC | 720 |
| TAAAAACTGG | TCAATAGCTA | CTCCTAGCTC | AAAGTTCAGC | CTGTCCAAGG | GCAAATTAAC | 780 |
| ATTTAAAGCT | TTCCCCCCAC | ATAATTCAAG | CAAAGCAGCT | GCTAATGTAG | TTTTACCACT | 840 |
| ATCAATTGGT | CCTTTAAACA | GCCAGTATCT | TTTTTTAGGA | ATGTTGTACA | CCATGCATTT | 900 |
| TAAAAAGTCA | TACACCACTG | AATCCATTTT | GGGCAACAAA | CAGTGTAGCC | AAGCAACTCC | 960 |
| AGCCATCCAT | TCTTCTATGT | CAGCAGAGCC | TGTAGAACCA | AACATTATAT | CCATCCTATC | 1020 |
| CAAAAGATCA | TTAAATCTGT | TTGTTAACAT | TTGTTCTCTA | GTTAATTGTA | GGCTATCAAC | 1080 |
| CCGCTTTTTA | GCTAAAACAG | TATCAACAGC | CTGTTGGCAT | ATGGTTTTTT | GGTTTTTGCT | 1140 |
| GTCAGCAAAT | ATAGCAGCAT | TTGCATAATG | CTTTTCATGG | TACTTATAGT | GGCTGGGCTG | 1200 |
| TTCTTTTTTA | ATACATTTTA | AACACATTTC | AAAACTGTAC | TGAAATTCCA | AGTACATCCC | 1260 |
| AAGCAATAAC | AACACATCAT | CACATTTTGT | TTCCATTGCA | TACTCTGTTA | CAAGCTTCCA | 1320 |
| GGACACTTGT | TTAGTTTCCT | CTGCTTCTTC | TGGATTAAAA | TCATGCTCCT | TTAACCCACC | 1380 |
| TGGCAAACTT | TCCTCAATAA | CAGAAAATGG | ATCTCTAGTC | AAGGCACTAT | ACATCAAATA | 1440 |
| TTCCTTATTA | ACCCCTTTAC | AAATTAAAAA | GCTAAAGGTA | CACAATTTTT | GAGCATAGTT | 1500 |
| ATTAATAGCA | GACACTCTAT | GCCTGTGTGG | AGTAAGAAAA | AACAGTATGT | TATGATTATA | 1560 |
| ACTGTTATGC | CTACTTATAA | AGGTTACAGA | ATATTTTTCC | ATAATTTTCT | TGTATAGCAG | 1620 |
| TGCAGCTTTT | TCCTTTGTGG | TGTAAATAGC | AAAGCAAGCA | AGAGTTCTAT | TACTAAACAC | 1680 |
| AGCATGACTC | AAAAAACTTA | GCAATTCTGA | AGGAAAGTCC | TTGGGGTCTT | CTACCTTTCT | 1740 |

-continued

```
CTTCTTTTTT GGAGGAGTAG AATGTTGAGA GTCAGCAGTA GCCTCATCAT CACTAGATGG    1800

CATTTCTTCT GAGCAAAACA GGTTTTCCTC ATTAAAGGCA TTCCACCACT GCTCCCATTC    1860

ATCAGTTCCA TAGGTTGGAA TCTAAAATAC ACAAACAATT AGAATCAGTA GTTTAACACA    1920

TTATACACTT AAAAATTTTA TATTTACCTT AGAGCTTTAA ATCTCTGTAG GTAGTTTGTC    1980

CAATTATGTC ACACCACAGA AGTAAGGTTC CTTCACAAAG ATCAAGTCCA AACCACATTC    2040

TAAAGCAACG AAGCAGTAGC AATCAACCCA CACAAGTGGA TCTTTCCTGT ATAATTTTCT    2100

ATTTTCATGC TTCATCCTCA GTAAGCACAG CAAGCATATG CAGTTAGCAG ACATTTTCTT    2160

TGCACACTCA GGCCATTGTT TGCAGTACAT TGCATCAACA CCAGGATTTA AGGAAGAAGC    2220

AAATACCTCA GTTGCATCCC AGAAGCCTCC AAAGTCAGGT TGATGAGCAT ATTTTACTCC    2280

ATCTTCCATT TTCTTGTACA GAGTATTCAT TTTCTTCATT TTTTCTTCAT CTCCTCCTTT    2340

ATCAGGATGA AACTCCTTGC ATTTTTTTAA ATATGCCTTT CTCATCAGAG GAATATTCCC    2400

CCAGGCACTC CTTTCAAGAC CTAGAAGGTC CATTAGCTGC AAAGATTCCT CTCTGTTTAA    2460

AACTTTATCC ATCTTTGCA                                                 2479
```

(2) INFORMATION FOR SEQ ID NO: 5:

(i) SEQUENCE CHARACTERISTICS:
        (A) LENGTH: 312 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 5:

```
TTTACCACTC CCTATCAGTG ATAGAGAAAA GTGAAAGTCG AGTTTACCAC TCCCTATCAG     60

TGATAGAGAA AAGTGAAAGT CGAGTTTACC ACTCCCTATC AGTGATAGAG AAAAGTGAAA    120

GTCGAGTTTA CCACTCCCTA TCAGTGATAG AGAAAGTGA AAGTCGAGTT TACCACTCCC     180

TATCAGTGAT AGAGAAAAGT GAAAGTCGAG TTTACCACTC CCTATCAGTG ATAGAGAAAA    240

GTGAAAGTCG AGTTTACCAC TCCCTATCAG TGATAGAGAA AAGTGAAAGT CGAGCTCGGT    300

ACCCGGGTCG AG                                                        312
```

MAMMALIAN PROTEIN INTERACTION CLONING SYSTEM

This is a continuation-in-part of application Ser. No. 09/050,863, filed Mar. 30, 1998, now U.S. Pat. No. 6,114,111.

FIELD OF THE INVENTION

The present invention is directed to compositions and methods for a genetic system of detecting protein-protein interactions in a mammalian host cell. The protein interactions are detected by using fusion proteins whose expression and interaction with each other results in transcriptional activation.

BACKGROUND OF THE INVENTION

Protein-protein interactions are of paramount and fundamental interest in biological systems. These interactions are involved in a wide variety of important biological reactions, including the assembly of enzyme subunits, in antigen-antibody reactions, in supramolecular structures of ribosomes, filaments, and viruses, in recognition and transport, in transcription regulation, and in ligand-receptor interactions. In addition, the area of protein-protein interactions has received significant attention in the area of signal transduction and biochemical pathway analysis.

Traditionally, protein-protein interactions were evaluated using biochemical techniques, including chemical cross-linking, co-immunoprecipitation and co-fractionation and -purification. Recently genetic systems have been described to detect protein-protein interactions. The first work was done in yeast systems, and was termed the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463.

However, while the yeast system works well, it is unsuitable for use in mammalian systems for a variety of reasons. Furthermore, the existing mammalian two-hybrid systems are neither suitable for a wide variety of cells, nor flexible, as they generally require quite highly specialized conditions. In addition, the existing mammalian two-hybrid systems are generally transient systems, rather than stable systems. Finally, these systems tend to have high background signals from non-specific interactions, giving rise to "false positives".

A number of factors make a flexible mammalian two-hybrid system highly desirable. First of all, post-translatonal modifications of proteins may contribute significantly to their ability to interact, yet mammalian cells have different post-translational modification systems than yeast. Thus, proteins that interact in a yeast system may not interact with the same specificity or avidity when placed in a mammalian cell. Similarly, proteins that would interact with correct post-translational processing may not be identified in a yeast system. In addition, a mammalian two-hybrid system that could be used in a wide variety of mammalian cell types would be highly desirable, since the regulation, induction, processing, etc. of specific proteins within a particular cell type can vary significantly; it would thus be a distinct advantage to assay for relevant protein-protein interactions in the relevant cell type. For example, proteins involved in a disease state could be tested in the relevant disease cells, resulting in a higher chance of identifying important protein interactions. Similarly, for testing of random proteins, assaying them under the relevant cellular conditions will give the highest chance of positive results. Furthermore, the mammalian cells can be tested under a variety of experimental conditions that may affect intracellular protein-protein interactions, such as in the presence of hormones, drugs, growth factors and cytokines, cellular and chemical stimuli, etc., that may contribute to conditions which can effect protein-protein interactions. In particular, a mammalian protein interaction cloning system is useful to identify candidate bioactive agents that have the potential to modulate a given protein-protein interaction.

Thus, a robust and adaptable mammalian two-hybrid system which can work in a wide variety of mammalian cell types is highly desirable.

Accordingly, it is an object of the invention to provide compositions and methods useful in a two-hybrid system which can be utilized reproducibly and stably in mammalian cells.

SUMMARY OF THE INVENTION

The invention provides compositions and methods useful in a mammalian two hybrid system for the detection of protein-protein interactions.

In one aspect of the invention, the invention provides compositions comprising a bait vector and a test vector. The bait vector comprises a first selection gene, a bait vector viral origin of replication which requires a bound viral replication protein to effect replication, and a first fusion gene. The fusion gene comprises a first sequence encoding a nucleic acid binding domain, and a second sequence comprising either a sequence encoding a bait protein or a cloning sequence comprising at least one cloning site. The test vector comprises a second selection gene, a test vector viral origin of replication which requires a bound viral replication protein to effect replication, and a second fusion gene. The second fusion gene comprises a third sequence encoding a transcriptional activation domain, and a fourth sequence comprising either a sequence encoding a test protein or a cloning sequence comprising at least one cloning site.

In a further aspect, the compositions further comprise a reporter vector comprising a first detectable gene, a viral replication protein gene, and an operator site, which upon binding of the nucleic acid binding domain and the transcriptional activation domain due to a protein-protein interaction of the bait protein and the test protein, will activate transcription of the first detectable gene and the viral replication protein gene.

In a further aspect, the invention provides compositions comprising a retroviral bait vector comprising a first fusion gene and an optional selection gene, and a retroviral test vector comprising a second fusion gene and an optional selection gene. The composition may further comprise a retroviral reporter vector comprising a first detectable gene and an operator site.

In an additional aspect, the invention provides mammalian host cells containing the compositions of the invention, optionally stably integrated into their chromosomes.

In a further aspect, the invention provides methods for detecting an interaction between a bait protein and a test protein comprising providing a mammalian host cell comprising a bait vector, a test vector, and a reporter vector, which may or may not be retroviral vectors. The host cell is subjected to conditions under which the first fusion gene and the second fusion gene are expressed to produce a first fusion protein and a second fusion protein. The method further comprises determining whether a protein-protein interaction between the first fusion protein and the second fusion protein occurred.

In a further aspect, the invention provides methods for isolating the test protein. The sequence encoding the test protein is isolated. Sequences encoding the full-length protein are also isolated.

In a further aspect, the invention provides methods for screening for bioactive agents that have the potential to modulate the protein-protein interaction between a bait protein and a test protein. These methods comprise (1) providing a mammalian host cell comprising a vector composition comprising genes encoding a bait protein, a test protein and a reporter protein, (2) subjecting the host cell to conditions under which the genes are expressed, producing a bait protein, a test protein and a reporter protein, (3) determining whether a protein-protein interaction between the bait protein and the test protein occurred by determining expression of the reporter protein, (4) adding candidate bioactive agents that are capable of modulating this protein-protein interaction, (5) determining the effect of the candidate bioactive agents on the protein-protein interaction between the bait protein and the test protein by determining expression of the reporter protein and (6) identifying the candidate bioactive agents.

BRIEF DESCRIPTION OF THE DRAWINGS

FIG. 1 depicts two reporter vectors as described in the Example.

FIG. 2 depicts the identification of JUN/FOS interactions using the methods and compositions of the invention. The Y axis depicts luciferase activity.

FIG. 3 depicts a preferred embodiment of the present invention.

FIG. 4 schematically depicts the requirements and results of the system.

FIG. 5 schematically depicts the method for screening for bioactive agents capable of modulating the protein-protein interaction between a bait protein and a test protein.

FIGS. 5A, 5B, and 5C schematically depict the method for screening for antagonistic bioactive agents using a host cell showing high level of reporter protein expression. 5A. The candidate bioactive agent is not modulating the protein-protein interaction between the bait protein and the test protein and the high level of reporter protein expression is not affected. 5B and 5C. The candidate bioactive agent is modulating the protein-protein interaction between the bait protein and the test protein, resulting in the loss of reporter protein expression.

FIGS. 5D and 5E schematically depict the method for screening for agonistic bioactive agents using a host cell showing low level of reporter protein expression. 5D. The candidate bioactive agent is not modulating the protein-protein interaction between the bait protein and the test protein and the low level of reporter protein expression is not affected. 5E. The candidate bioactive agent is modulating the protein-protein interaction between the bait protein and the test protein, resulting in the increased reporter protein expression. b, bait protein; d, DNA binding domain; a, transcriptional activation domain; t, test protein; r, reporter protein; c, candidate bioactive agent.

DETAILED DESCRIPTION OF THE INVENTION

As outlined herein, the present invention is directed to compositions and methods useful as a mammalian two-hybrid system. While the basic mechanism is similar to the yeast two hybrid system based on transcription activation, the present invention can be used in any number of mammalian cells, is highly stable, and is designed to reduce the background signals frequently found in other systems. The present invention thus provides a robust and versatile system to evaluate protein-protein interactions in a wide variety of mammalian cells under any number of different conditions.

Briefly, transcription can be activated through the use of two functional domains of a transcription activator protein; a domain or sequence of amino acids that recognizes and binds to a nucleic acid sequence, i.e. a nucleic acid binding domain, and a domain or sequence of amino acids that will activate transcription when brought into proximity to the target sequence. Thus the transcriptional activation domain is thought to function by contacting other proteins required in transcription, essentially bringing in the machinery of transcription. It must be localized at the target gene by the nucleic acid binding domain, which putatively functions by positioning the transcriptional activation domain at the transcriptional complex of the target gene.

These two domains can be either from the same transcriptional activator protein, or can be from different proteins (see McKnight et al., Proc. Natl. Acad. Sci. USA 89:7061 (1987); Ghosh et al., J. Mol. Biol. 234(3):610–619 (1993); and Curran et al., 55:395 (1988)). A variety of transcriptional activator proteins comprising an activation domain and a binding domain are known in the art, as is described below.

Thus, in the two-hybrid system, a first protein, or "bait protein", as termed herein, is fused to a nucleic acid binding domain of a nucleic acid binding protein, such as a transcriptional activator protein, and a second protein, or "test protein", is fused to the activator domain of a transcriptional activator. If the bait protein and the test protein bind, i.e. have a specific protein-protein interaction, the activator domain is brought into position near the nucleic acid binding domain, and transcription of a reporter gene (sometimes referred to herein as detectable gene) occurs. If there is little or no interaction, there is little or no reporter protein (sometimes referred to herein as detectable protein) made.

The invention is generally described as follows. In the preferred embodiment of the present invention, the mammalian two-hybrid system comprises three components: a bait vector, a test vector, and a reporter vector. The bait vector has a viral origin of replication that requires the presence of a viral replication protein to effect replication, a selection gene, and a first fusion construct comprising a nucleic acid binding domain from a transcriptional activator protein fused to a "bait" protein; that is, a protein for which a protein-protein interaction is sought. The test vector also has a viral origin of replication which requires a viral replication protein and a selection gene, and further comprises a second fusion construct comprising a transcriptional activation domain fused to a "test" protein; that is, a protein which potentially binds to the bait protein. The reporter construct comprises a reporter gene, a viral replication protein gene, and a regulatory site such as an operator. Upon binding of the nucleic acid binding domain and the transcriptional activation domain, due to a protein-protein interaction of the bait and test proteins, the operator is activated and will cause increased transcription of the reporter gene and the viral replication protein gene. The viral replication protein can then bind to the viral origin of replication on the bait and test vectors to permit replication of the vector, ensuring survival of the cell due to the selection gene. The detectable or reporter gene then serves as the basis of a sorting or screening system to isolate cells which have a protein-protein interaction, and the test protein is identified and characterized as desired. As is more fully described below, once the protein-protein interaction between the bait and test proteins is established, candidate bioactive agents that are to be evaluated for their potential to modulate, either directly or indirectly, this protein-protein interaction are added to the host cells. The modulation of this bait protein-test protein interaction leads to either an increase or decrease of transcription of the reporter gene and subsequently results in a detectable increase or decrease of reporter protein expression which is measured by reporter protein activity. The change of reporter protein expression or reporter protein activity is determined anew and thus bioactive agents which modulate an interaction between a bait protein and a test protein are identified.

Accordingly, the present invention provides compositions comprising three components: a bait vector, a test vector, and a reporter vector. By "vector" or "episome" herein is meant a replicon used for the transformation of host cells. The vectors may be either self-replicating extrachromosomal vectors ("plasmids") or vectors which integrate into a host genome. A preferred embodiment utilizes retroviral vectors, as is more fully described below.

For non-retroviral embodiments, suitable vectors are derived from any number of known vectors, including, but not limited to, pCEP4 (Invitrogen), pCl-NEO (Promega), and pBl-EGFP (Clontech). Basically, any mammalian expression vectors with strong promoters such as CMV can be used to construct test or bait vectors.

Generally, these expression vectors include transcriptional and translational regulatory nucleic acid operably linked to nucleic acids which are to be expressed. "Operably linked" in this context means that the transcriptional and translational regulatory nucleic acid is positioned relative to any coding sequences in such a manner that transcription is initiated and translation of the protein is assured. Generally, this will mean that the promoter and transcriptional initiation or start sequences are positioned 5' to the coding region. The transcriptional and translational regulatory nucleic acid will generally be appropriate to the host cell used, as will be appreciated by those in the art. Numerous types of appropriate expression vectors, and suitable regulatory sequences, are known in the art for a variety of host cells.

In general, the transcriptional and translational regulatory sequences may include, but are not limited to, promoter sequences (including CAAT box and TATA box), ribosomal binding sites (including internal ribosome entry sites (IRES)), transcriptional start and stop sequences (including mRNA polyadenylation sequence 5'-AATAAA-3'), RNA splicing sequences, translational start and stop sequences (including 5' and 3' untranslated regions, initiator codon (ATG), Kozak consensus sequence (5'-A/GNNATGG-3') and nonsense codons (UAA, UAG, UGA)), either constitutive or inducible enhancer, activator or repressor sequences (located either upstream, downstream or overlapping relative to promoter and being either cell-line dependent, tissue-specific or temporally dependent), and protein targeting signals (including signals for endoplasmatic reticulum retention and extracellular secretion, signals for localization to plasma membranes, peroxisomes, nucleus, mitochondria, lysosomes, golgi complex and focal adhesions). In a preferred embodiment, the regulatory sequences include a promoter and transcriptional start and stop sequences.

Promoter sequences include constitutive and inducible promoter sequences. The promoters may be either naturally occurring promoters, hybrid or synthetic promoters. Hybrid promoters, which combine elements of more than one promoter, are also known in the art, and are useful in the present invention.

In general, the vectors of the present invention utilize two different types of promoters. In a preferred embodiment, the promoters on the bait and test vectors are constitutive, and drive the expression of the fusion proteins and selection genes, if applicable, at a high level. However, it is possible to utilize inducible promoters for the fusion constructs, if necessary, for example if toxic proteins are used as either the bait or test proteins.

Preferred promoters for driving expression of the fusion constructs, and the selection genes, if applicable, on the bait and test vectors, include, but are not limited to, cytomegaloviral promoters (CMV; Boshart et al., Cell, 41:521–530 (1985)), SV40 (Lusky and Botchan, Nature 283:253 (1931)), SRα (Takebe et al., Mol. Cell. Biol. 8:466 (1988)), Rous sarcoma viral promoters (RSV; Gorman et al., Proc. Natl. Acad. Sci. USA 79:6777–6781 (1981)), thymidine kinase (TK; Wigler et al., Cell 11:223 (1977)), β-globin, EF-1a (Mizushima and Nagata, Nucl. Acids Res. 18:5322 (1990), UbC (Wulff et al., FEBS Letters 261:101–105 (1990), etc. Particularly preferred promoters are CMV promoters. Preferred retroviral promoters are discussed below.

In a preferred embodiment, the promoter on the reporter vector is associated with at least one copy of the bait fusion protein binding site, such as an operator as defined below, and is essentially an inducible promoter. Induction in this case comprises a protein-protein interaction of the bait and test proteins sufficient to cause the association of the nucleic acid binding domain and the transcriptional activator domain resulting in transcription activation. What is important is that the promoter-operator system (i.e. the minimal promoter) on the reporter construct does not result in transcription unless the protein-protein interaction is present, although as will be appreciated by those in the art, there may be some low level of background constitutive expression.

In addition, the expression vector may comprise additional elements such as a viral origin of replication, selection genes, etc., as is more fully described below.

In a preferred embodiment, the integrating vector may be directed to a specific locus in the host cell by selecting the appropriate homologous sequence for inclusion in the vector. For integrating expression vectors (non-retroviral), the expression vector generally contains at least one sequence homologous to the host cell genome, and preferably two homologous sequences which flank the expression construct. Constructs for integrating vectors are well known in the art. As for all of the vectors described herein, the vector may be extrachromosomal, or may be integrated into the genome of the host cell.

In a preferred embodiment, one or more of the vectors may contain a RNA splicing sequence upstream or downstream of the test or bait protein gene to increase the level of gene expression. See Barret et al., Nucleic Acids Res. 1991; Groos et al., Mol. Cell. Biol. 1987; and Budiman et al., Mol. Cell. Biol. 1988.

In a preferred embodiment, either the vector (particularly the test vector) or one or both of the fusion constructs may contain a "rescue" sequence. A rescue sequence is a sequence (either nucleic acid or amino acid) which may be used to purify or isolate either the test or bait proteins or the nucleic acid encoding them. Thus, for example, protein rescue sequences include purification sequences such as the $His_6$ tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, IacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the sequence encoding the test protein is isolated by a PCR method. As is outlined below, should the rescued test protein sequence encode a fragment of the full-length test protein, numerous suitable methods for the subsequent isolation of the full-length protein encoding sequence are known in the art. The nucleic acid sequence of the rescued nucleic acid sequence is determined.

In a preferred embodiment, one or more retroviral vectors are used. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins—gag, pol, and env—that are required for packaging, processing, reverse transcription, and integration of recombinant genomes. Those RNA molecules that have in cis the Ψ packaging signal are packaged into maturing virions.

Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express. In addition, transfection efficiencies can be extremely high, thus obviating the need for selection genes in some cases.

A particularly well suited retroviral transfection system is described in Mann et al., supra: Pear et al., PNAS USA 90(18):8392-6 (1993); Kitamura et al., PNAS USA 92:9146–9150(1995); Kinsella et al., Human Gene Therapy 7:1405–1413; Hoffmann et al., PNAS USA 93:5185–5190; Choate et al., Human Gene Therapy 7:2247 (1996); WO 94/19478; PCT US97/01019, and references cited therein, all of which are incorporated by reference.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing fusion constructs at uniformly high levels; and promoters driving expression of a second gene, placed in sense or anti-sense relative to the 5' LTR.

Preferred vectors include a vector based on the murine stem cell virus (MSCV) (see Hawley et. al., Gene Therapy 1:136 (1994)) and a modified MFG virus (Rivere et al., Genetics 92:6733 (1995)), and pBABE (see PCT US97/01019, incorporated by reference).

As for the other vectors, the retroviral vectors may include inducible and constitutive promoters. Constitutive promoters are preferred for the bait and test vectors, and include, but are not limited to, CMV, SV40, Srα, RSV, EF-1a, UbC and TK. Similarly, the reporter vector promoter is associated with at least one copy of an operator, as outlined herein. As for the other vectors, the retroviral vectors may comprise a variety of transcriptional and translational regulatory sequences and at least one cloning site for the subcloning of at least one recombinant DNA fragment.

In addition, it is possible to configure a retroviral vector to allow expression of bait genes or test genes after integration of a bait or test vector in target cells. For example, Tet-inducible retroviruses can be used to express bait or test genes (Hoffman et al., Proc. Natl. Acad. Sci. USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In general, three types of vectors are used in the present invention. The first is a bait vector, generally comprising a first selection gene, a viral origin of replication which requires a bound viral replication protein to effect replication, and a first fusion gene.

Selection genes allow the selection of transformed host cells containing the vector, and particularly in the case of mammalian cells, ensures the stability of the vector, since cells which do not contain the vector will generally die. Selection genes are well known in the art and will vary with the host cell used. By "selection gene" herein is meant any gene which encodes a gene product that confers resistance to a selection agent. Suitable selection agents include, but are not limited to, neomycin (or its analog G418), blasticidin S, histinidol D, bleomycin, puromycin, hygromydin B, and other drugs.

In a preferred embodiment more than one vector or retroviral vector is transfected into the same host cell. In order to assure presence and stability of each vector, each individual vector may confer resistance to a different selection agent and thus may comprise a different selection gene. Subsequently the host cell may be exposed to at least two selection agents and the surviving cells will show resistance to at least two selection agents. The use of one or more selection agents and one or more selection genes is well known in the art.

In some cases, for example when using retroviral vectors, the requirement for selection genes is lessened due to the high transformation efficiencies which can be achieved. Accordingly, selection genes need not be used in retroviral constructs, although they can be. In addition, when retroviral vectors are used, the bait and test vectors may also contain detectable genes as are described below rather than selection genes; it may be desirable to verify that the vector is present in the cell, but not require selective pressure for maintenance.

In one embodiment, the bait vector also comprises a viral origin of replication which requires a bound viral replication protein to effect replication. As is known in the art, the only extrachromosomal vectors which replicate in mammalian cells are virally derived. A number of viral origin of replications require the binding of a specific viral replication protein to effect replication. Suitable origin of replication/viral replication protein pairs include, but are not limited to, the Epstein Barr origin of replication (SEQ ID NO:1) and the Epstein Barr nuclear antigen (SEQ ID NO:2; see Sugden et al., Mole. Cell. Biol. 5(2):410–413 (1985)); the SV40 origin of replication (SEQ ID NO:3) and the SV40 T antigen (SEQ ID NO:4; see Margoiskee et al., Mole. Cell. Biol. 8(7):2837 (1988)). The bait vector origin of replication and the test vector origin of replication are preferably the same, but as will be appreciated in the art, can be different.

As is described herein, the coding sequence for the viral replication protein can be on the reporter construct, or on either of the bait or test vectors, or both. In a preferred embodiment, the coding sequence for the viral replication protein is on the reporter construct, as this will serve to decrease the background signal and false positives. This serves as a second reporter gene, effectively, as the plasmids are not replicated unless the bait protein and the test protein interact sufficiently to cause transcription of the viral replication protein; it is a selection, of sorts, since the lack of ones or the other of the bait and test vectors will generally be fatal to the cell, due to the loss of the selection gene. In an alternate embodiment, the viral replication protein coding sequence may be contained on either or both of the bait vector and the test vector, for instance when false positives are not a concern, when the reporter carries another drug selection to ensure its stable integration into the cell, or when an additional reporter gene is desirable. That is, if the viral replication protein is on the bait and/or test vectors, another reporter gene such as luciferase can be used in addition to the first reporter gene.

In addition, the bait vector comprises a first fusion gene. By "fusion gene" or "fusion construct" herein is meant nucleic acid that comprises at least two functionally distinct sequences; i.e. generally sequences from two different genes. As will be appreciated by those in the art, in some embodiments the sequences described herein may be DNA, for example when extrachromosomal plasmids are the vectors, or RNA, for example when retroviral vectors are used. Generally, the sequences are directly linked together without any linking sequences, although in some embodiments linkers such as restriction endonuclease cloning sites or linkers encoding flexible amino acids such as glycine and serine linkers such as are known in the art are used. In a preferred embodiment, the first fusion gene comprises a first sequence encoding a nucleic acid binding domain, and the second sequence encodes a bait protein. By "nucleic acid binding domain" herein is meant a proteinaceous domain which is able to bind a specific nucleic acid sequence, generally a DNA sequence. As noted above, transcriptional activation proteins generally contain at least two domains, a nucleic acid binding domain and a transcriptional activation domain; for the purposes of the present invention, the nucleic acid binding domain and the transcriptional activation domain may come from the same protein or different proteins. As will be appreciated by those in the art, what is important is that the transcriptional activator from which these sequences are derived have functionally distinct domains. Suitable nucleic acid binding domains include, but are not limited to, nucleic acid binding domains from Tet, GAL4 (amino acids 1–147; Fields et al., supra; see also Gill et al., Proc. Natl. Acad. Sci. USA 87:2127 (1990); Chasman et al., Mol. Cell. Biol. 9:4746 (1989)); LexA (Thliveris et al., Proc. Natl. Acad. Sci. USA 1992; Hurstels et al., EMBO J. 1986); GCN4 from S. cerevisiae (Hope et al., Cell 46:885 (1986)); ARD1 from S. cerevisiae (Thukral et al., Mol. Cell. Biol. 9:2360 (1989), the human estrogen receptor (Kumar et al., Cell 51:941 (1987), and NF-kB p65, and p53, and derivatives thereof which are functionally similar.

In a preferred embodiment, the first fusion gene further comprises a second sequence encoding a bait protein. "Protein" in this context includes peptides, oligopeptides and proteins. By "bait protein" herein is meant a protein which is to be tested for interaction with another protein. Generally, the bait protein comprises all or part of a target molecule which has either been implicated in a biological process of interest or for which the function is sought. Suitable bait proteins include functional domains of a wide variety of proteins, including, but not limited to, receptors, ligands, protein hormones, enzymes (particularly proteases), antibodies, antigens, nucleic acid processing proteins, transcription proteins, etc. In addition, the bait protein may also be a random protein, for example of from about 2 amino acids to about 100 amino acids, with from about 10 to about 50 amino acids being preferred. In one embodiment, the bait protein is fully randomized, with no sequence preferences or constants at any position. In a preferred embodiment, the protein is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histiclines for phosphorylation sites, etc., or to purines, or to reduce the chance of creation of a stop codon, etc.

In a preferred embodiment, the bias is towards peptides or nucleic acids that interact with known classes of molecules. For example, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumor and anti-microbial activity. Short peptide fragments of a protein kinase C isozyme ($\beta$PKC), have been shown to block nuclear translocation of $\beta$PKC in Xenopus oocytes following stimulation. And, short SH-3 target peptides have been used as pseudosubstrates for specific binding to SH-3 proteins. This is of course a short list of available peptides with biological activity, as the literature is dense in this area. Thus, there is much precedent for the potential of small peptides to have activity on intracellular signaling cascades, In addition, agonists and antagonists of any number of molecules may be used as the basis of biased randomization of test proteins as well.

Customarily one bait protein is used to test a library of test sequences as is described below; however, as will be appreciated by those in the art, the bait protein may be one of a library as well, thus forming an experimental matrix wherein two libraries (although the coding regions of the libraries could be identical) are evaluated for protein-protein interactions.

As described herein, bait proteins are preferably fused to the nucleic acid binding domains, arid, as described further below, the test proteins are preferably fused to the transcriptional activation domains. However, as will be appreciated by those in the art, the bait proteins may be fused to the transcriptional activation domains, and the test proteins may be fused to the nucleic acid binding domains.

In a preferred embodiment, self-activating bait proteins are filtered out from the bait protein library.

The present invention also provides test vectors. The test vector also generally comprises a selection gene, although as outlined above, this may not be necessary in some embodiment, for example if the test vector is a retroviral vector, or if the test vector is combined with another vector. Preferably, when the bait and test vectors are distinct, the selection gene of the test vector is different from the selection gene of the bait vector, to ensure that both vectors are maintained within the cell. However, in some embodiments this may not be required; accordingly, the first and second selection genes may be the same or different. The test vector also comprises a viral origin of replication, as described above.

The test vector further comprises a second fusion gene comprising a third sequence encoding a transcriptional activator domain and a fourth sequence encoding a test protein. As above, these may be fused directly or via a linker. By "transcriptional activator domain" or "transcriptional activation domain" or grammatical equivalents herein is meant a proteinaceous domain which is able to activate transcription.

Suitable transcription activator domains include, but are not limited to, transcriptional activator domains from GAL4, GCN4, ARD1, the human estrogen receptor, VP16 (Triezenberg et al., Genes Dev. 2(6):718–729 (1988)), and 842 (Gyuris et al, Cell 1993), and NF-kB p65, and derivatives thereof which are functionally similar.

The fourth sequence encodes a test protein. By "test protein" herein is meant a candidate protein which is to be tested for interaction with a bait protein. Protein in this context means proteins, oligopeptides, and peptides, i.e. at least two amino acids attached.

In a preferred embodiment, the test protein sequence is one of a library of test protein sequences; that is, a library of test proteins is tested for binding to one or more bait proteins. The test protein sequences can be obtained from genomic DNA, cDNA or can be random sequences. Alternatively, specific classes of test proteins may be tested. The library of test proteins or sequences encoding test proteins are incorporated into a library of test vectors, each or most containing a different test protein sequence. Preferably a library of test protein sequences or a sequence encoding a test protein is fused to a transcriptional activation domain and tested against a bait protein fused to a nucleic acid binding domain. However, as will be appreciated by those in the art, a library of test protein sequences or a sequence encoding a test protein can also be fused to the nucleic acid binding domain and tested against a bait protein fused to the transcriptional activation domain.

In a preferred embodiment, the test protein sequences are obtained from genomic DNA sequences. Generally, as will be appreciated by those in the art, genomic digests are cloned into test vectors. The genomic library may be a complete library, or it may be fractionated or enriched as will be appreciated by those in the art.

In a preferred embodiment, the test protein sequences are obtained from cDNA libraries. A cDNA library from any number of different cells or organisms may be used, and cloned into test vectors. As above, the cDNA library may be a complete library, or it may be fractionated or enriched in a number of ways.

In a preferred embodiment, the test protein sequences are random sequences. Generally, these will be generated from chemically synthesized oligonucleotides. Generally, random test proteins range in size from about 2 amino acids to about 100 amino acids, with from about 10 to about 50 amino acids being preferred. As above, fully random or "biased" random proteins may be used.

As above, in some embodiments the second fusion gene comprises a third sequence encoding a transcriptional activator domain and a cloning sequence comprising at least one cloning site for insertion of nucleic acid encoding a test protein.

The present invention also provides reporter vectors. In a preferred embodiment, the reporter vector comprises an operator site, a first detectable gene and a viral replication protein gene.

By "operator" herein is meant a nucleic acid sequence, generally DNA, to which the nucleic acid binding domain of the first fusion protein, which includes the bait protein, binds. Upon binding of the first fusion protein to the operator, and protein-protein interaction between the bait protein and the test protein which is fused to the transcriptional activation domain, the transcriptional activation domain is brought into promoter proximity. The transcriptional activation domain will then activate transcription of the reporter gene(s) and viral replication protein gene, if present. Protein-protein interaction between bait and test protein may also occur prior to binding of the nucleic acid binding domain to the operator.

In a preferred embodiment, the nucleic acid sequence (the "binding sequence" or "binding site") which binds the nucleic acid binding domain is repeated within the operator. Thus, an operator preferably has at least one binding site, with at least about 3 binding sites being preferred, and at least about 5 being especially preferred.

Preferred operator sequences include, but are not limited to, tetracycline responsive element (TRE; SEQ ID NO:5; Gossen et al., Proc. Natl. Acad. Sci. USA 89(12):5547–5551 (1992)), LexA, Gal 4 binding sites, p53 binding sites, etc.

Thus, the operator functions essentially as an activated or inducible promoter, wherein activation comprises the presence of a sufficiently strong interaction of the bait and test protein to cause localization of the transcriptional activator domain at the operator site.

In a preferred embodiment, the operator can activate transcription bidirectionally so that two reporter genes can be placed on the same vector. That is, when the operator is used to activate more than one gene, the operator is preferably positioned between the minimal promoters controlling the expression of the reporter genes, i.e. between the coding region for a detectable gene and the coding region for a viral replication protein, if present. Alternatively, in another embodiment, the coding region for the two genes is present in an operon motif, with the single operator driving transcription of a single message containing more than one gene.

The reporter vector further comprises at least one reporter gene, which is transcribed upon activation of the operator, due to a protein-protein interaction of the bait and test proteins. In other words, expression and measurable activity of a reporter protein is dependent on the interaction of the bait protein with the test protein which subsequently results in the transcriptional activation of the reporter gene followed by the translation of the respective mRNA. By "reporter gene" or "detectable gene" herein is meant a gene whose expression results in a detectable or reportable phenotype, either by itself or with the addition of a compound or substance. By "reporter protein" or "detectable protein" herein is meant the protein encoded by the reporter gene or detectable gene. Suitable reporter proteins include, but are not limited to, green fluorescent protein and derivatives, luciferase, alkaline phosphatase, chloramphenicol acetyl transferase, IacZ, and drug selection genes (preferably other than those on the bait and test vectors may also be used). The monitoring of reporter protein expression is well known in the art. In a preferred embodiment, the expression of the detectable gene allows for cell sorting, such as by fluorescence-activated cell sorting, or FACS.

In a preferred embodiment, green fluorescent protein (GFP) or any of its derivatives including, but not limited to, EGFP (Haas et al., Curr. Biol. 6:315–324 (1996)), d2EGFP (Clontech), EBFP (Clontech), GFPuv (Crameri et al., Nature Biotechnol. 14:315–319 (1996)), BFP (blue fluorescent protein), YFP (yellow fluorescent protein) and RFP (red fluorescent protein) is used as a reporter protein. GFP expression and loss of GFP expression can be monitored noninvasively in vivo in individual cells.

In a preferred embodiment, the reporter vector comprises a viral replication protein gene. Upon activation of the operon, transcription of a viral replication protein gene results in a viral replication protein which can then bind to the viral origin of replication, causing replication of the vectors containing the origin of replication. This functions to provide a second reporter to reduce the background or "false positives", particularly when the test and bait vectors comprise selectable marker genes, since the absence of vector replication will result in cell death. Suitable viral proteins are outlined above.

In some embodiments, for example when retroviral bait and test vectors are used, the reporter vector does not need a viral replication protein gene, as retroviral vectors integrate into the host chromosome.

Generally, the bait vector, the test vector and the reporter vector are distinct vectors, although as will be appreciated by those in the art, one, two or three independent vectors may be used. That is, the components of the bait and test vectors could reside on a single vector or on two vectors Similarly, the reporter vector can be independent or part of either the bait or test vector, or the entire system may reside on a single vector, if the size of the vector is not a concern. Generally, when the test protein is a member of a library, as is outlined below, the test vector will be separate from the bait and reporter vectors.

In a preferred embodiment, e.g., when the subject method is used in combination with a defined (or single) bait protein and a defined (or single) test protein, the individual components (i.e., the bait protein encoding gene and the test protein encoding gene) reside on one vector while the reporter gene resides on another vector.

In another preferred embodiment, the individual components, e.g., genes encoding the bait protein, the test protein and the reporter protein may reside on one vector. As will be appreciated by those in the art, all combinations are possible and accordingly, as used herein, this combination of components, contained within one or more vectors, which may be retroviral or not, is referred to herein as a "vector composition".

The compositions of the invention may be packaged into kits, or transformed into cells to detect protein-protein interactions.

In a preferred embodiment, for example, when the compositions are to be used in kits, the first fusion gene comprises a first sequence encoding a nucleic acid binding domain and a cloning sequence comprising at least one cloning site for insertion of nucleic acid sequences encoding a bait protein. Similarly and as described herein, the second fusion gene comprises a sequence encoding a transcriptional activation domain and a cloning sequence comprising at least one cloning site for insertion of nucleic acid sequences encoding a test protein. In this embodiment, the end user of the kit will insert the nucleic acid sequences encoding the bait and test proteins into the vector(s). Suitable cloning sites are well known in the art. As outlined herein, the end user can fuse the bait protein to either nucleic acid binding domain or transcriptional activation domain and the test protein to either transcriptional activation domain or nucleic acid binding domain.

In a preferred embodiment, bait and test vectors comprising cloning sites for the insertion of bait and test proteins are included in kits useful in the detection of protein-protein interactions in mammalian host cells. The kits may also include the reporter vector, or mammalian host cells as outlined herein. In a preferred embodiment, the host cell already contains at least the reporter vector, preferably integrated. In one embodiment, the kit comprises a container or receptacle with single or multiple aliquots of the bait, test and reporter vectors. Other compounds, buffers, enzymes, or reagents may also be included in the kit. The kit may have additional packaging or compounds such as tubes, beakers, holders, pipettes, buffers, salts, acids or bases. The kit may also include materials for polyacrylamide or agarose gels, as well as materials for detecting labels, if used. In some embodiments, the kit contains primers, templates or both.

In a preferred embodiment, the compositions are introduced into mammalian host cells to screen for protein-protein interactions. By "introduced into" or grammatical equivalents herein is meant that the nucleic acids enter the cells in a manner suitable for subsequent expression of the nucleic acid. The vectors can be introduced simultaneously, or sequentially in any order. The method of introduction is largely dictated by the targeted cell type and the composition of the vector. Exemplary methods include $CaPO_4$ precipitation, liposome fusion, lipofectin®, electroporation, viral infection, etc. The vectors may stably integrate into the genome of the host cell (for example, with retroviral introduction, outlined herein), or may exist either transiently or stably in the cytoplasm (i.e. through the use of traditional plasmids, utilizing standard regulatory sequences, selection markers, etc.).

As will be appreciated by those in the art, the type of cells used in the present invention can vary widely. Basically, any mammalian cells may be used, with mouse, rat, primate and human cells being particularly preferred. Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH 3T3 cells, CHO, Cos, etc. See the ATCC cell line catalog, hereby expressly incorporated by reference.

In one embodiment, the cells may be genetically engineered, that is, contain exogenous nucleic acid in addition to the vectors of the invention.

In a preferred embodiment, the compositions of the invention are stably integrated into the genome of the host cell by non-homologous recombination and expression of the bait protein, test protein and reporter protein is determined. Usually vectors, not including a targeting sequence which directs site-specific integration, integrate randomly into the genome of the host cell and thus individual cells may show variation in protein expression, depending on how efficient each bait protein encoding gene, test protein encoding gene and reporter protein encoding gene is transcribed. However, a clonal cell line obtained by cell cloning techniques and further propagation should show a consistent level of protein expression, i.e. each individual cell should express the bait protein, the test protein and the reporter protein at a very similar level.

Alternatively, in a homologous recombination/integration event, the transfected DNA is targeted to a specified genomic locus where it recombines in a homologous fashion with its chromosomal equivalents. Briefly, a recombinant DNA molecule is constructed wherein the gene(s) of interest which is (are) to be integrated (e.g., the bait protein and the test protein encoding genes) is (are) flanked by regions of complete homology, often of considerable length, of a target genomic locus. Such a recombinant molecule, upon transfection into a host cell, undergoes homologous recombination in the two flanking regions such that the interior portion of the target genomic locus is recombined out and replaced by the gene of interest (e.g, the bait protein and test protein encoding genes). Due to the nature of this recombination/integration event, usually sequences within the recombinant molecule flanking the gene(s) of interest region, are lost. Although the frequency of such homologous recombination/integration events is quite low, by employing appropriate selection and screening protocols, one can detect the homologous recombination event and subsequently isolate, propagate and further analyze or manipulate the homologously recombined cell. Appropriate selection and screening protocols are known to those in the art and are found in e.g., Mansour et al., *Cell,* 51:503 (1988) and Murray, *Gene Transfer and Expression Protocols, Methods in Molecular Biology,* Vol. 7 (Clifton: Humana Press, 1991).

In a preferred embodiment, host cells which have the compositions of the invention integrated into their genome are screened for expression of the reporter protein and based on reporter protein expression they may be categorized as low-expressing, moderate-expressing or high-expressing host cell lines. Host cells may be also categorized as low-expressing, moderate-expressing or high-expressing host cell lines simply based on the strength of the protein-protein interaction between a bait protein and a test protein, i.e., based on the affinity that a bait protein has for a test protein. As understood by those in the art, if the affinity of a bait protein for a test protein is low it may persist only temporarily and the transcriptional activation domain may not be retained for a long time at the transcriptional complex. Such a low affinity or temporarily interaction will ultimately result in a low-level expression of the respective reporter gene. Alternatively, if the interaction between a bait protein and a test protein is strong, i.e., a high affinity exists between a bait protein and a test protein, the interaction may be more persistent and the transcriptional activation domain will be retained for a longer time at the transcriptional complex. Such a strong or more persistent interaction will ultimately result in a high-level expression of the respective reporter gene.

In a preferred embodiment, host cells containing the reporter construct are generated first, and preferably the reporter vector is integrated into the genome of the host cell, for example, using a retroviral reporter vector. In a preferred embodiment, the bait vector may be integrated as well. To this end, the bait and reporter vectors may be contained on a single construct.

Once the components of the system are in the host cell, the cell is subjected to conditions under which the selectable markers and fusion proteins are expressed. If a test protein has sufficient affinity to the bait protein to activate transcription, the viral replication protein and the detectable, protein is produced, and cells containing these proteins will survive drug selection and can be detected as outlined above. The detectable protein will be produced at a measurably higher level than in the absence of a protein-protein interaction. Thus the determination of a protein-protein interaction is generally done on the basis of the presence or absence of the detectable genes. Preferably positive controls comprising proteins known to associate with the bait protein are run, as well as negative controls comprising proteins known not to associate with the bait protein.

In a preferred embodiment, once a cell with an altered phenotype is detected, the cell is isolated from the plurality which do not have altered phenotypes. This may be done in any number of ways, as is known in the art, and will in some instances depend on the assay or screen. Suitable isolation techniques include, but are not limited to, drug selection, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes; changes in fluorescent characteristics, etc. The preferred isolation techniques are drug selection and FACS based on the expression of the detectable gene, with a preferred embodiment utilizing both simultaneously.

Once a cell with a protein-protein interaction is detected and isolated, it is generally desirable to identify the test protein (and the bait protein, if its identity was unknown). In a preferred embodiment, the test protein nucleic acid and/or the test protein is isolated from the positive cell. This may be done in a number of ways. In a preferred embodiment, primers complementary to DNA regions common to the vector, or to specific components of the library such as a rescue sequence, defined above, are used to "rescue" the unique test sequence. Alternatively, the test protein is isolated using a rescue sequence. Thus, for example, rescue sequences comprising epitope tags or purification sequences may be used to pull out the test protein, using immunopredpitation or affinity columns. In some instances, as is outlined below, this may also pull out the bait protein, if there is a sufficiently strong binding interaction between them. Alternatively, the test protein may be detected using mass spectroscopy.

Once rescued, the sequence of the test protein and/or test nucleic acid is determined. Often, when genomic libraries or cDNA libraries or DNA fragments obtained thereof are employed in the screening method outlined herein (or in any other screening method) the nucleic acid sequence encoding the test protein is not full-length, i.e., the nucleic acid sequence does not encode the complete test protein. By "full-length" cDNA, gene, mRNA, RNA or grammatical equivalents herein is meant any nucleic acid which encodes a complete protein. In addition to the complete protein encoding sequence, a full-length cDNA, gene, mRNA or RNA may optionally contain 5' and 3' untranslated nucleic acid sequences. The complete protein may include amino acids incorporated by translation of the corresponding mRNA, that may subsequently be eliminated from the native protein, e.g. signal peptide sequences or sequences involved in protein splicing and protein processing. By "full-length protein" or grammatical equivalents herein is meant a protein encoded by a full-length cDNA, gene, RNA or mRNA. As appreciated by those in the art, full-length proteins may include post translationally modifications, including, but not limited to, signal peptide cleavage, protein splicing, protein precursor processing, glycosylation, and the like. Accordingly, a "partial cDNA", "partial gene", "partial mRNA", "partial RNA" or a "partial protein" or grammatical equivalents are meant to indicate a cDNA, gene, mRNA, RNA or a protein which represents a portion of a full-length cDNA, gene, mRNA, RNA or a protein. Accordingly in a preferred embodiment, the determined nucleic acid sequence information of the rescued partial protein will be used to isolate the full-length coding sequence of the test protein. The isolation and characterization of a full-length coding sequence using a partial sequence information is well known in the art This information can then be used in a number of ways.

In a preferred embodiment, the test protein is resynthesized and reintroduced into the host cells, to verify the effect. These cells may be the same as in the original experiment or different. This, may be done using retroviruses, or alternatively using fusions to the HIV-1 Tat protein, and analogs and related proteins, which allows very high uptake into target cells. See for example, Fawell et al., Proc. Natl. Acad. Sci. USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment the test protein which is reintroduced into a host cell to verify the protein-protein interaction with the bait protein, is the full-length protein, as described above. However, sometimes it may be desired to modify the full-length protein, e.g., to delete certain amino acid sequences from the full-length protein that may otherwise target the full-length protein to a specific, however not desired, cellular or extracellular location. These sequences include, but are not limited to, signal peptides for extracellular secretion and amino acid sequences targeting the protein to the endoplasmatic reticulum, golgi complex, focal adhesions, lysosomes, peroxisomes and plasma membranes.

Alternatively, in a preferred embodiment, targeting sequences such as a nuclear translocation signal (e.g., SV40 Large T; Fischer-Fantuzzi and Vesc, Mol. Cell. Biol. 108:1657–1664 (1989)) may be added to the protein of interest in order to target it to the nucleus where transcription occurs.

In a preferred embodiment, the bait or test protein is a wild-type or naturally occurring sequence. Alternatively, the test or bait protein may be a derivative protein, that is, it may contain amino acid substitutions, insertions or deletions, or combinations thereof. Thus, included within the definition of test and bait proteins are amino acid substitutions, insertions, and deletions. Similarly, further included within the definition of bait and test proteins are fragments, or less-than-full-length proteins. These modifications are routinely performed by in vitro mutagenesis of the nucleic acid encoding the protein of interest. In vitro mutagenesis methods are well known to those in the art and are found in, for example, Sambrook et al., *Molecular Cloning: A Laboratory Manual* (New York: Cold Spring Harbor Laboratory Press, 1989) and Ausubel et al., Short Protocols in Molecular Biology (John Wiley & Sons, Inc., 1995).

In a preferred embodiment the full-length test protein (including derivatives) is reintroduced into a host cell, comprising a bait vector and a reporter vector. The protein-protein interaction between bait protein and full-length test protein is determined by measuring the reporter protein as described above.

Once a protein-protein interaction is determined, the test protein may be used in a method for screening for candidate bioactive agents that modulate this interaction. The bait and test proteins subject to these screening methods can be proteins originally identified through the subject matter of this invention. However, the protein-protein interaction between any known proteins, as described in the literature, may be subject to the screening method described herein.

In a preferred embodiment, the nucleic acids encoding test and/or bait proteins are used to express the respective recombinant protein (also referred to as protein of interest). A variety of expression vectors, including viral and non-viral expression vectors can be made which are useful for recombinant protein expression in a variety of systems, including, but not limited to, yeast, bacteria, archaebacteria, fungi, insect cells and animal cells, including mammalian cells.

The expressed protein may also be expressed as a fusion protein, including fusion to tag polypeptides or fusions to other protein sequences. Recombinant protein is produced by culturing a host cell transformed with a nucleic acid encoding the protein of interest (generally as an expression vector), under the appropriate conditions that induce or cause expression of the protein.

In a preferred embodiment, the recombinant protein is purified following expression. Numerous suitable methods for recombinant protein expression, including generation of expression vectors, generation of fusion proteins, introducing expression vectors into host cells, protein expression in host cells, and purification methods are known to those in the art and are described, for example, in the following textbooks: Sambrook et al., *Molecular Cloning: A Laboratory Manual* (New York: Cold Spring Harbor Laboratory Press, 1989), Ausubel et al., *Short Protocols in Molecular Biology* (John Wiley & Sons, Inc., 1995), Harlow and Lane, *Antibodies: A Laboratory Manual* (New York: Cold Spring Harbor Laboratory Press, 1988), O'Reilly et al., *Baculovirus Expression Vectors: A Laboratory Manual* (New York: Oxford University Press, 1994), Richardson, *Baculovirus Expression Protocols* (Totowa: Humana Press, 1995), Kriegler, *Gene Transfer and Expression: A Laboratory Manual* (New York: Oxford University Press, 1991), Roth, *Protein Expression in Animal Cells*, Methods in Cell Biology Vol. 43 (San Diego: Academic Press, 1994), Murray, *Gene Transfer and Expression Protocols, Methods in Molecular Biology*, Vol. 7 (Clifton: Humana Press, 1991 ), Deutscher, *Guide to Protein Purification, Methods in Enzymology* Vol. 182 (San Diego: Academic Press, Inc., 1990), Harris and Angal, *Protein Purification Methods: A Practical Approach* (Oxford: IRL Press at Oxford University Press, 1994), Harris and Angal, *Protein Purification Applications: A Practical Approach* (Oxford: IRL Press at Oxford University Press, 1990), Rees et al., *Protein Engineering: A Practical Approach* (Oxford: IRL Press at Oxford University Press, 1992) and White, *PCR Protocols, Methods in Molecular Biology*, Vol. 15 (Totowa, Humana Press, 1993).

In a preferred embodiment, the recombinant test and bait proteins are used in in vitro binding assays to confirm the protein-protein interaction between bait and test protein first occurred within the host cell.

Generally, in a preferred embodiment of the methods herein, the bait protein is non-difusably bound to an insoluble support having isolated sample receiving areas (e.g. a microtiter plate, an array, etc.). The insoluble supports may be made of any composition to which the bait protein can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the bait protein is not crucial so long as it is compatible with the reagents and overall methods of the invention, maintains the characteristics of the bait protein and is nondiffusable. The bait protein may be either bound directly to the insoluble support (e.g. via cross-linking) or indirectly (e.g., via antibody, other protein or nucleic acid, etc.). Preferred methods of binding include the use of antibodies (which do not sterically block this protein-protein interaction surface for the test protein and preferably are directed against a tag polypeptide which may be incorporated into the recombinant bait protein), direct binding to "sticky" or ionic supports, chemical crosslinking, etc. Following binding of the bait protein, excess unbound material is removed by washing. The sample receiving areas may then be blocked through incubation with bovine serum albumin (BSA), casein or other innocuous protein.

The test protein is added to the binding assay. Determination of the binding of the test protein to the bait protein may be done using a wide variety of assays, including labeled in vitro protein-protein binding assays, electrophoretic mobility shift assays (EMSA), immunoassays for protein binding, functional assays (phosphorylation assays, etc.) and the like. (e.g., see, Harlow and Lane, *Antibodies: A Laboratory Manual* (New York, Cold Spring Harbor Laboratory Press, 1988) and Ausubel et al., *Short Protocols in Molecular Biology* (John Wiley & Sons, Inc., 1995).

By "labeled" herein is meant that the compound (e.g., the protein which is tested for binding) is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and anudigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the test protein may be labeled at tyrosine positions using $^{125}I$, or at methionine positions using $^{35}S$, or with fluorophores. Alternatively, more than one component may be labeled with different labels using $^{125}I$ or $^{35}S$ for one protein, for example, and a fluorophor for a potential additional component.

In a preferred embodiment, the test protein is labeled, and binding is determined directly. For example, this may be done by attaching all or a portion of the bait protein to a solid support, adding a labeled test protein (for example a fluorescent label), washing off excess reagent, and determining whether the label is present on the solid support. Various blocking and washing steps may be utilized as is known in the art.

In another preferred embodiment, the test and bait proteins are combined first and after a certain incubation period, one protein, preferably the non-labeled protein (e.g. the bait protein) is bound either directly or indirectly to an insoluble support. The second protein, preferably labeled (e.g., the test protein) which is bound to the first protein is visualized in accordance with the label incorporated.

In a preferred embodiment, the invention provides methods for screening for bioactive agents that are capable of modulating the protein-protein interaction between the bait protein and the test protein.

The term "candidate bioactive agent" or "bioactive agent" as used herein describes any molecule, e.g., protein, small organic molecule, polysaccharide, lipid, polynucleotide, etc., or mixtures thereof with the capability of directly or indirectly modulating the protein-protein interaction between a bait protein and a test protein. Of particular interest are bioactive agents that either have a low or no toxicity for human cells. Candidate agents may be added as individual agents, as combined samples of individual agents or as more complex libraries as is discussed further below. Generally a plurality of assay mixtures is run in parallel with different bioactive agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemicals groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines and derivatives, structural analogs or combinations thereof. Particularly preferred are peptides. In fact, virtually any small organic molecule that is potentially capable of binding to a biological target molecule of interest may find use in the present invention provided that it is sufficiently soluble and stable in aqueous solutions to be tested for its ability to bind to the biological target molecule.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homophenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of prokaryotic and eukaryotic proteins may be made. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each peptide consists of essentially random amino acids. Since generally these random peptides are chemically synthesized, they may incorporate any amino acid at any position. The synthetic process can be designed to generate randomized proteins to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or the like.

In a preferred embodiment a library of protein encoding nucleotide sequences is added to the host cell comprising the vector composition of the invention. The library of protein encoding nucleotide sequences may be obtained from genomic DNA, from cDNAs or from random nucleotides. Particularly preferred in this embodiment are libraries encoding bacterial, fungal, viral, and mammalian proteins and peptides, with the latter being preferred, and human encoding proteins and peptides being especially preferred. As described above and as known in the art the protein and peptide encoding nucleotide sequences may be inserted into any vector suitable for expression in mammalian cells.

In a preferred embodiment, the candidate bioactive agents are obtained from combinatorial chemical libraries, a wide variety of which are available in the literature. By "combinatorial chemical library" herein is meant a collection of diverse chemical compounds generated in a defined or random manner, generally by chemical synthesis. Millions of chemical compounds can be synthesized through combinatorial mixing.

In a preferred embodiment, the invention provides methods for screening for bioactive agents that are capable of modulating the protein-protein interaction between the bait protein and the test protein. "Modulating the protein-protein interaction between the bait protein and the test protein" includes an increase (i.e., tighter affinity between bait protein and test protein), a decrease (i.e., lower affinity between bait protein and test protein), or a change in the type or kind of this protein-protein interaction.

Addition of the candidate bioactive agent is performed under conditions which allow the modulation of the protein-protein interaction to occur. As will be appreciated by those in the art, those conditions will depend upon the nature of the protein-protein interaction, the nature of the candidate bioactive agent, and are determined routinely and empirically, as will the concentration of the candidate bioactive agents to be employed. Thus, in this embodiment, the candidate bioactive agent possesses a size or structure which allows binding to either the bait protein or test protein (although this may not be necessary), and modulate the protein-protein interaction between these proteins. This modulation preferably results in a measurable change of reporter protein expression.

Accordingly, in this embodiment, the methods comprise (1) providing a mammalian host cell comprising a vector composition, comprising a first fusion gene encoding a bait protein, a second fusion gene encoding a test protein and a reporter gene. This vector composition, as outlined herein, may or may not comprise retroviral vectors, and may or may not be integrated into the genome of the host cell. (2) The host cells is subjected to conditions under which the first fusion gene (i.e., the bait protein encoding gene), the second fusion gene (i.e., the test protein encoding gene) and the reporter gene are expressed to produce a first fusion protein (i.e., the bait protein), a second fusion protein (i.e., the test protein) and a reporter protein. Optionally, it is determined (3) whether a protein-protein interaction between the bait protein and the test protein occurred by determining expression of the reporter protein. (4) Candidate bioactive agents that are capable of modulating this protein-protein interaction are added. Simultaneously, sequentially or at a later step (5) the effect of the candidate bioactive agents on the protein-protein interaction between the bait protein and the test protein is determined by detecting the expression of the reporter protein. Preferably, (6) the candidate bioactive agents are identified. Bioactive agents identified by the subject methods may find use as new small molecule drug leads, enzyme inhibitors, diagnostic, reagents, and the like.

As outlined above and as known to those in the art, several reporter genes may be used to monitor the modulation of the protein-protein interaction between the bait protein and the test protein. In a preferred embodiment, GFP expression is used to monitor this change of protein-protein interaction between the bait protein and the test protein noninvasively in vivo in individual cells.

In a preferred embodiment, it is desired to screen for bioactive agents that are antagonists, i.e., the libraries of bioactive agents is used to identify bioactive agents that decrease the protein-protein interaction between the bait protein and the test protein. In this embodiment, preferably, a mammalian host cell which is categorized as a high expressing cell line (as outlined above) is provided. Using this host cell in the present invention, it is possible to identify in a background of high GFP expressing cells individual cells which either express low level of GFP or which completely lost GFP expression. Thus, monitoring GFP expression allows for the detection of either reduced GFP expression or loss of GFP expression in a single host cell which is due to a candidate bioactive agent decreasing the protein-protein interaction between a bait protein and a test protein. The host cell is identified and propagated for further analysis.

In a preferred embodiment, it is desired to screen for bioactive agents that are agonists, i.e., the libraries of bioactive agents is used to identify bioactive agents that increase the protein-protein interaction between the bait protein and the test protein. In this embodiment, preferably, a mammalian host cell which is categorized as a low expressing cell line (as outlined above) is provided. Using this host cell in the present invention, it is possible to identify in a background of low GFP expressing cells individual cells which express high levels of GFP. Thus, monitoring GFP expression allows for the detection of increased GFP expression in a single host cell which is due to a candidate bioactive agent increasing the protein-protein interaction between a bait protein and a test protein. The host cell is identified and propagated for further analysis.

In a preferred embodiment, the candidate bioactive agent is a protein which is encoded by a cDNA, cDNA fragment or genomic DNA fragment (for example, as part of a CDNA or genomic library) and is readily identified by rescuing the nucleic acid encoding the candidate bioactive agent. The nucleic acid sequence is determined. As outlined above, the obtained information is used to isolate a full-length cDNA encoding the full-length candidate bioactive agent and to express the candidate bioactive agent as a recombinant protein. Preferably, the full-length recombinant candidate bioactive agent(either in form of a full-length cDNA or as a full-length protein) may be purified, labeled and used in in vivo and in in vitro binding assays (as outlined above) to confirm its modulation of the protein-protein interaction between a bait and a test protein as was originally observed in a host cell.

In a preferred embodiment, the identified candidate bioactive agent is tested for its possible binding to either the test protein or the bait protein, using in vitro binding assays outlined above.

In a preferred embodiment, the modulation of the protein-protein interaction between a bait protein and a test protein by a candidate bioactive agent is optimized. The identified candidate bioactive agent is either chemically modified or the nucleic acid encoding the candidate bioactive agent is subjected to in vitro mutagenesis. These modifications result in the synthesis of candidate bioactive agent variants. Preferably, these variants are purified, labeled and used in in vivo and in in vitro binding assays (as outlined above) to test their modulation of the protein-protein interaction between a bait and a test protein. These variants lead either to more potent, more tolerable or less toxic small molecule drug leads, enzyme inhibitors, diagnostic reagents, and the like.

In a preferred embodiment, the efficacy of the candidate bioactive agent variant (i.e., its characteristics, its modulation of the protein-protein interaction between the bait protein and the test protein, its binding to either the bait protein or test protein, etc.) is compared to the efficacy of the originally isolated candidate bioactive variant using in vitro binding assays and in vivo assays (as outlined herein). In this embodiment, the in vitro binding assays comprise at least four components: a bait protein, a test protein, an originally identified candidate bioactive agent and a candidate bioactive agent variant.

In one embodiment, a bait protein is bound to an insoluble support and a test protein, which may be labeled, is added and allowed to bind to the bait protein. Incubations are performed at any temperature which facilitates optimal binding, typically between 4° C. and 40° C. Incubation periods are selected for optimum binding, but are also optimized to facilitate rapid high through put screening. Typically between 0.1 and 1 hour is sufficient. Excess labeled test protein is generally removed or washed away. The original candidate bioactive agent or a variant thereof is then added, and the presence or absence of the labeled test protein in the wash solution or supernatant is followed, to indicate a possible displacement by the candidate bioactive agent or its variant.

In this embodiment, displacement of the test protein is an indication that the candidate bioactive agent or a variant thereof is modulating the protein-protein interaction between the bait protein and the test protein and thus functions as antagonist. A displacement of more test protein by the candidate bioactive agent variant (i.e., when compared to the original candidate bioactive agent) indicates that the variant is a stronger antagonist which may be developed as a more potent small molecule drug lead, enzyme inhibitor, diagnostic reagent, or the like. Alternatively, a displacement of less test protein by the candidate bioactive agent variant (i.e., when compared to the original candidate bioactive agent) which indicates that the variant is a weaker antagonist can lead to the development of a more tolerable or less toxic small molecule drug lead, enzyme inhibitor, diagnostic reagent, or the like.

In another embodiment, the original candidate bioactive agent or a variant thereof is added first to the bait protein which is bound to an insoluble support, with incubation and washing, followed by the test protein, which may be labeled, with incubation and washing. Absence of binding of the test protein or reduced binding thereof when compared to a control sample may indicate that the original bioactive agent is bound to the bait protein with a high affinity and may mask the protein-protein interaction surface for the test protein. Alternatively, the original candidate bioactive agent may have changed the tertiary structure of the bait protein and thereby rendered the bait protein unable to functionally interact with the test protein. More or less binding of the test protein, when used in combination with the candidate bioactive agent variant (and when compared to the original candidate bioactive agent) indicates a weaker or stronger binding of the variant to the bait protein. The ramifications drawn, are similar to those outlined above.

In an alternative embodiment, the original candidate bioactive agent or a variant thereof is aided first to the test protein which is bound to an insoluble support, with incubation and washing, followed by the bait protein, which may be labeled, with incubation and washing. Absence of binding of the bait protein or reduced binding thereof when compared to a control sample may indicate that the original candidate bioactive agent or a variant thereof is bound to the test protein with a high affinity and may mask the protein-protein interaction surface for the bait protein. Alternatively, the original candidate bioactive agent or a variant thereof have changed the tertiary structure of the test protein and thereby rendered the test protein unable to functionally interact with the bait protein. More or less binding of the bait protein, when used in combination with the candidate bioactive agent variant (and when compared to the original candidate bioactive agent) indicates a weaker or stronger binding of the variant to the test protein. The ramifications drawn, are similar to those outlined above. As described above, numerous and suitable in vitro binding assays and variations of the assays outlined herein are known to those in the art.

In a preferred embodiment, either the test protein or the nucleic acid encoding it is used to identify other target molecules, i.e. the initially identified test protein is then used as a bait protein. It is also possible to synthetically prepare labeled proteins and use them to screen a cDNA library expressed in bacteriophage for those cDNAs which bind the protein.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Plasmid Construction

Reporter Vector

Full length EBNA gene coding region was amplified by polymerase chain reaction from plasmid pCEP4, purchased from Invitrogen. The EBNA fragment was then cloned into pCR2.1. Plasmid pBI-EGFP was purchased from Clontech. The EBNA fragment was transferred from pCR2.1 vector into Mlu I-Nhe I gap of pBI-EGFP to construct pBI-R, the bi-directional double reporter vector. A control vector pBI-EGFP-Luc was also purchased from Clontech with pBI-EGFP. This vector vias used in quantitative luciferase assay. The test and bait vectors were made in a similar manner, as will be appreciated by those in the art. Vector maps were shown in FIG. 1.

Cell Culture and Transfection

Phoenix (293 origin; see PCT/US97/01019, hereby incorporated expressly by reference in its entirety) cells were used in all of the transient assays; however, as will be appreciated, integrated reporter constructs can be made and are generally preferable. Cells were grown up in DMEM plus 10% fetal bovine serum. Plasmids were co-transfected into cells by $Ca^{2+}$ transfection method. GFP fluorescence was visible 20 hours after transfection. In FIG. 2, pCl-neo was used to balance total DNA used in control transfection. pTBIND is a vector expression a Tet DNA binding domain only. pVACT is a vector expression VP16 activation domain only. pTFOS is a vector expressing Tet-FOS fusion protein. pVJUN is a vector expression VP16-JUN fusion protein. All of the above expression vectors use CMV promoters. 3 $\mu$g of pTBIND, or pTFOS, or pVACT or pVJUN was used in transfection of each 10 cm plate as indicated in FIG. 2 (Bars). 0.5 $\mu$g of pBI-EGFP-Luc was used in transfection of a 10 cm plate for luciferase assay. 0.5 $\mu$g of pBI-R was used in GFP color assay (Pictures). Luciferase assay was done 40 hours after transfection using Promega luciferase assay kit and a Victor 1420 multilabel counter (Wallac).

Column 1 is the reporter vector pBIR only. Column 2 is the reporter vector plus the bait vector pTBIND and the test vector pVACT. Column 3 is pTFOS, pVACT and the reporter vector. Column 4 is pTFOS and pVACT and the reporter vector, co-transfected. Only column 4 shows significant luciferase activity above background, which indicates FOS/JUN interaction detected by the mammalian protein interaction cloning system.

We claim:

1. A method for detecting an interaction between a bait protein and a test protein comprising:
    a) providing a mammalian host cell comprising:
        i) a bait vector comprising:
            1) a first selection gene;
            2) a bait vector viral origin of replication which requires a bound viral replication protein to effect replication; and
            3) a first fusion gene comprising:
                A) a first sequence encoding a nucleic acid binding domain; and
                B) a second sequence encoding a bait protein;
        ii) a test vector comprising:
            1) a second selection gene;
            2) a test vector viral origin of replication which requires a bound viral replication protein to effect replication; and
            3) a second fusion gene comprising:
                A) a third sequence encoding a transcriptional activation domain; and
                B) a fourth sequence encoding a test protein; and
        iii) a reporter vector comprising:
            1) a first reporter gene;
            2) a gene encoding a viral replication protein that binds to said viral origin of replication; and
            3) an operator site, to which said nucleic acid binding domain binds;
    b) subjecting the host cell to conditions under which the first fusion gene and the second fusion gene are expressed to produce a first fusion protein and a second fusion protein;
    c) determining whether a protein-protein interaction between said first fusion protein and said second fusion protein occurred; and
    d) isolating said fourth sequence.

2. A method for detecting an interaction between a bait protein and a test protein comprising:
    a) providing a mammalian host cell comprising:
        i) a retroviral bait vector comprising a first fusion gene comprising:
            1) a first sequence encoding a nucleic acid binding domain; and
            2) a second sequence encoding a bait protein;

ii) a retroviral test vector comprising a second fusion gene comprising:
1) a third sequence encoding a transcriptional activation domain; and
2) a fourth sequence encoding a test protein; and
iii) a retroviral reporter vector comprising:
1) a first reporter gene; and
2) an operator site, to which said nucleic acid binding domain binds;
b) subjecting the host cell to conditions under which the first fusion gene and the second fusion gene are expressed to produce a first fusion protein and a second fusion protein;
c) determining whether a protein-protein interaction between said first fusion protein and said second fusion protein occurred; and
d) isolating said fourth sequence.

3. A method for detecting an interaction between a bait protein and a test protein comprising:
a) providing a mammalian host cell comprising:
i) a bait vector comprising:
1) a first selection gene;
2) a bait vector viral origin of replication which requires a bound viral replication protein to effect replication; and
3) a first fusion gene comprising:
A) a first sequence encoding a nucleic acid binding domain; and
B) a second sequence encoding a bait protein;
ii) a test vector comprising:
1) a second selection gene;
2) a test vector viral origin of replication which requires a bound viral replication protein to effect replication; and
3) a second fusion gene comprising:
A) a third sequence encoding a transcriptional activation domain; and
B) a fourth sequence encoding a test protein; and
iii) a reporter vector comprising:
1) a first reporter gene;
2) a gene encoding a viral replication protein that binds to said viral origin of replication; and
3) an operator site, to which said nucleic acid binding domain binds;
b) subjecting the host cell to conditions under which the first fusion gene and the second fusion gene are expressed to produce a first fusion protein and a second fusion protein;
c) determining whether a protein-protein interaction between said first fusion protein and said second fusion protein occurred; and
d) detennining said fourth sequence.

4. A method for detecting an interaction between a bait protein and a test protein comprising:
a) providing a mannnalian host cell comprising:
i) a retroviral bait vector comprising a first fusion gene comprising:
1) a first sequence encoding a nucleic acid binding domain; and
2) a second sequence encoding a bait protein;
ii) a retroviral test vector comprising a second fusion gene comprising:
1) a third sequence encoding a transcriptional activation domain; and
2) a fourth sequence encoding a test protein; and
iii) a retroviral reporter vector comprising:
1) a first reporter gene; and
2) an operator site, to which said nucleic acid binding domain binds;
b) subjecting the host cell to conditions under which the first fusion gene and the second fusion gene are expressed to produce a first fusion protein and a second fusion protein;
c) determining whether a protein-protein interaction between said first fusion protein and said second fusion protein occurred; and
d) determining said fourth sequence.

5. A method according to claim 1, further comprising using said fourth sequence to isolate nucleic acid encoding a full-length test protein.

6. A method according to claim 5, further comprising expressing said nucleic acid to generate a full-length recombinant test protein or derivative thereof.

7. A method according to claim 6, further comprising determining whether said full-length recombinant test protein or said derivative thereof interacts with said bait protein.

8. A method for screening for a bioactive agent capable of modulating a protein-protein interaction between a bait protein and a test protein comprising:
a) providing a mammalian host cell comprising a vector composition comprising:
i) a first fusion gene comprising:
1) a first sequence encoding a nucleic acid binding domain; and
2) a second sequence encoding a bait protein;
ii) a second fusion gene comprising:
1) a third sequence encoding a transcriptional activation domain; and
2) a fourth sequence encoding a test protein; and
iii) a reporter gene comprising:
1) a coding region for a reporter protein; and
2) an operator site, to which said nucleic acid binding domain binds;
b) subjecting the host cell to conditions under which the first fusion gene and the second fusion gene are expressed to produce a first fusion protein and a second fusion protein;
c) adding a candidate bioactive agent to said host cell; and
d) determining the effect of said candidate bioactive agent on the protein-protein interaction between said bait protein and said test protein.

9. A method according to claim 8, wherein said vector composition further comprises at least one selection gene.

10. A method according to claim 8, wherein said vector composition further comprises at least one origin of replication and at least one gene encoding a replication protein that binds to said origin of replication.

11. A method according to claim 8, further comprising identifying said candidate bioactive agent.

* * * * *

UNITED STATES PATENT AND TRADEMARK OFFICE
CERTIFICATE OF CORRECTION

PATENT NO. : 6,316,223 B1
DATED : November 13, 2001
INVENTOR(S) : Donald Payan et al.

It is certified that error appears in the above-identified patent and that said Letters Patent is hereby corrected as shown below:

Title page,
Item [56], under "References Cited - U.S. PATENT DOCUMENTS" after 5,667,973, change "9/1997" to -- 8/1997 --.

Column 6,
Line 17, change "(1931))," to -- (1981)), --.

Column 7,
Line 4, change "IacZ, to -- lacZ, --.

Column 9,
Line 11, change "Margoiskee" to -- Margolskee --.
Line 24, change "ones" to -- one --.

Column 10,
Line 32, change "histiclines" to -- histidines --.

Column 13,
Line 8, change "IacZ" to -- lacZ --.

Column 19,
Line 4, change "non-difusably" to -- non-diffusably --.

Column 26,
Line 2, change "vias" to -- was --.

Signed and Sealed this

Eleventh Day of June, 2002

Attest:

JAMES E. ROGAN
Attesting Officer     Director of the United States Patent and Trademark Office